United States Patent
Tanaka

(10) Patent No.: US 9,535,079 B2
(45) Date of Patent: Jan. 3, 2017

(54) SAMPLE PROCESSING SYSTEM AND CONTROLLING METHOD OF THE SAME

(75) Inventor: Hiroyuki Tanaka, Halstenbek (DE)

(73) Assignee: SYSMEX CORPORATION, Kobe (JP)

(*) Notice: Subject to any disclaimer, the term of this patent is extended or adjusted under 35 U.S.C. 154(b) by 76 days.

(21) Appl. No.: 12/589,908

(22) Filed: Oct. 29, 2009

(65) Prior Publication Data

US 2010/0112703 A1    May 6, 2010

(30) Foreign Application Priority Data

Oct. 30, 2008 (JP) .................................. 2008-280311

(51) Int. Cl.
| | |
|---|---|
| *G01N 35/04* | (2006.01) |
| *G01N 35/02* | (2006.01) |
| *G01N 35/00* | (2006.01) |

(52) U.S. Cl.
CPC ....... *G01N 35/00603* (2013.01); *G01N 35/026* (2013.01); *G01N 2035/0415* (2013.01); *Y10T 436/113332* (2015.01)

(58) Field of Classification Search
CPC .............................................. G01N 35/00603
See application file for complete search history.

(56) References Cited

U.S. PATENT DOCUMENTS

| | | |
|---|---|---|
| 6,444,171 B1 | 9/2002 | Sakazume et al. |
| 2002/0031837 A1* | 3/2002 | Matsubara ............. G01N 35/02 436/180 |
| 2008/0310999 A1 | 12/2008 | Yagi et al. |

FOREIGN PATENT DOCUMENTS

| | | | |
|---|---|---|---|
| EP | 1887356 A2 * | 2/2008 | |
| JP | 63-217273 | 9/1988 | |
| JP | 2000-046842 A | 2/2000 | |
| JP | 2003-066050 A | 3/2003 | |
| WO | WO 2004/013615 A1 | 2/2004 | |

* cited by examiner

*Primary Examiner* — Yelena G Gakh
*Assistant Examiner* — Michelle Adams
(74) *Attorney, Agent, or Firm* — Brinks Gilson & Lione

(57) ABSTRACT

A sample processing system is disclosed that comprises: a transportation apparatus configured to convey a sample container; a first analyzer, arranged along the transportation apparatus, configured to measure a sample accommodated in a sample container conveyed by the transportation apparatus; a second analyzer, arranged along the transportation apparatus, configured to measure a sample accommodated in a sample container conveyed by the transportation apparatus; and a transportation controller configured to determine an analyzer to which a sample container is conveyed, and to control the transportation apparatus to convey the sample container to the determined analyzer, wherein: the first analyzer is configured to conduct primary measurement; and the second analyzer is configured to conduct both primary measurement and review measurement.

21 Claims, 20 Drawing Sheets

| F1 | F2 | F3 |
|---|---|---|
| Measurement unit ID | Primary measurement | Review measurement |
| M1 | 1 | 0 |
| M2 | 1 | 0 |
| M3 | 1 | 1 |

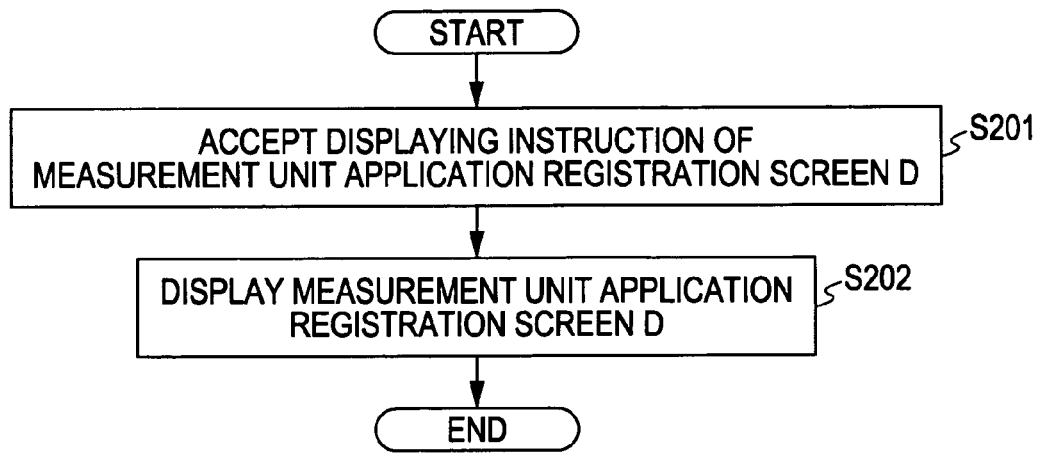
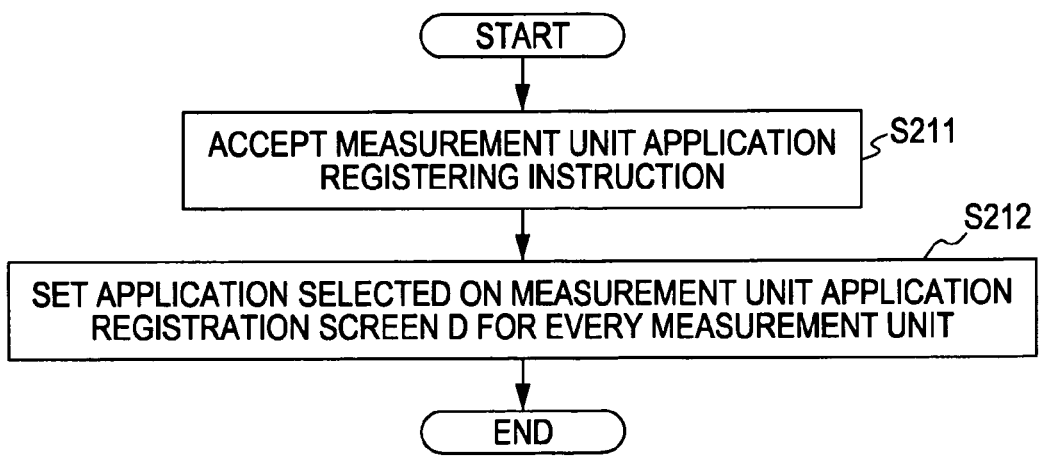

SAMPLE PROCESSING SYSTEM AND CONTROLLING METHOD OF THE SAME

RELATED APPLICATIONS

This application claims priority under 35 U.S.C. §119 to Japanese Patent Application No. 2008-280311 filed on Oct. 30, 2008, the entire content of which is hereby incorporated by reference.

FIELD OF THE INVENTION

The present invention relates to a sample processing system including a plurality of measurement units (analyzers) for measuring a sample and a transportation apparatus for conveying the sample to the measurement units, and a controlling method of the same.

BACKGROUND

A sample container accommodating a sample is automatically supplied to an analyzer, and the sample is continuously measured with the analyzer. A system having a configuration of arranging a sample sending device for temporarily accommodating and sending out the sample container to be supplied to the analyzer, a plurality of analyzers, and a sample receiving device for receiving and accommodating the sample container accommodating the measured sample, and connecting each device with a transportation apparatus for conveying the sample container, wherein the sample container is supplied to one of the analyzers from the sample sending device by the transportation apparatus to perform measurement, and the sample container after the measurement is accommodated in the sample receiving device is known. Such system is used to measure samples such as blood or urine, wherein reexamination (review measurement) is performed on the same sample if the result of the first measurement (primary measurement) with respect to the sample is determined as deviating from a normal range. When performing the review, the sample container accommodating the sample, which primary measurement is terminated, is automatically resupplied to the analyzer in the system (see e.g., Japanese Laid-Open Patent Publication No. 63-217273, and US Patent Application Publication No. 2008/310999).

In such system, an analyzer dedicated for review measurement is sometimes arranged separate from the analyzer used for the primary measurement. The review measurement thus can be rapidly conducted using the review measurement dedicated analyzer when an order of review measurement arises. However, in a test facility where the rate of review measurement tends to be low, the number of times the analyzer dedicated for review measurement of the plurality of analyzers conducts the measurement is significantly small compared to the number of times other analyzers conduct the primary measurement, and thus the time such analyzer is actually operating is short. In other words, the primary measurement, which occupies most of the measurement, concentrates on the analyzer dedicated for primary measurement, and the sample measurement ability of the analyzer dedicated for review measurement is not sufficiently utilized.

SUMMARY

The scope of the present invention is defined solely by the appended claims, and is not affected to any degree by the statements within this summary.

A first sample processing system embodying features of the present invention includes:
  a transportation apparatus configured to convey a sample container;
  a first analyzer, arranged along the transportation apparatus, configured to measure a sample accommodated in a sample container conveyed by the transportation apparatus;
  a second analyzer, arranged along the transportation apparatus, configured to measure a sample accommodated in a sample container conveyed by the transportation apparatus; and
  a transportation controller configured to determine an analyzer to which a sample container is conveyed, and controlling the transportation apparatus to convey the sample container to the determined analyzer,
  wherein:
  the first analyzer is configured to conduct primary measurement;
  the second analyzer is configured to conduct both primary measurement and review measurement;
  the transportation controller comprises a memory to store information that the first analyzer is for primary measurement and that the second analyzer is for both primary measurement and review measurement; and
  the transportation controller determines an analyzer to which the sample container is conveyed based on the information stored in the memory.

A second sample processing system embodying features of the present invention includes:
  a transportation apparatus configured to convey a sample container;
  a first analyzer, arranged along the transportation apparatus, configured to measure a sample accommodated in a sample container conveyed by the transportation apparatus;
  a second analyzer, arranged along the transportation apparatus, configured to measure a sample accommodated in a sample container conveyed by the transportation apparatus; and
  a transportation controller configured to determine an analyzer to which a sample container is conveyed, and to control the transportation apparatus to convey the sample container to the determined analyzer,
  wherein:
  the first analyzer is configured to conduct primary measurement;
  the second analyzer is configured to conduct both primary measurement and review measurement; and
  the transportation controller controls the transportation apparatus to convey the sample container to the first or the second analyzer when the sample accommodated in the sample container is a target of primary measurement, and controls the transportation apparatus to convey the sample container to the second analyzer when the sample accommodated in the sample container is a target of review measurement.

A first controlling method of a transportation apparatus in a sample processing system comprising,
  a transportation apparatus for conveying a sample container,
  a first analyzer, arranged along the transportation apparatus, configured to measure a sample accommodated in a sample container conveyed by the transportation apparatus, the first analyzer being configured to conduct primary measurement, a second analyzer, arranged along the transportation apparatus, configured to measure a sample accommodated in a sample container conveyed by the transportation apparatus, the second analyzer being configured to conduct both primary measurement and review measurement, and a transportation controller for controlling the conveying operation of a sample container by the transportation apparatus, the method embodying features of the present invention includes:

storing, by the transportation controller, information that the first analyzer is for the primary measurement and that the second analyzer is for both the primary measurement and the review measurement;

receiving an order of the primary measurement or an order of the review measurement related to the sample accommodated in the sample container at the transportation controller;

determining an analyzer to which the sample is conveyed based on the information stored by the transportation controller in the storing step and the order of measurement received by the receiving step; and controlling the transportation apparatus to convey the sample container to the analyzer determined in the determining step.

BRIEF DESCRIPTION OF THE DRAWINGS

FIG. 11 is a flowchart showing a procedure of a displaying process of a measurement unit application registration screen of the system controller;

FIG. 12 is a flowchart showing a procedure of the measurement unit application registration process of the system controller;

DETAILED DESCRIPTION OF THE PREFERRED EMBODIMENTS

The preferred embodiment of the present invention will be described with reference to the drawings. In the present embodiment, "primary measurement" refers to conducting a measurement on a specific measurement item by using a sample collected from a patient, such as initial screening test, or first run. "Review measurement" refers to conducting a measurement on a measurement item common with the primary measurement or a certain measurement item relevant to the measurement item of the primary measurement by using the remains of the sample used in the primary measurement, such as reflex test, or second run. The review measurement is sometimes conducted when the measurement result of the primary measurement is not within a normal range, or when a result greatly different from the tendency of the past measurement result for the same patient is obtained.

[Configuration of Sample Processing System]

Figure 1:
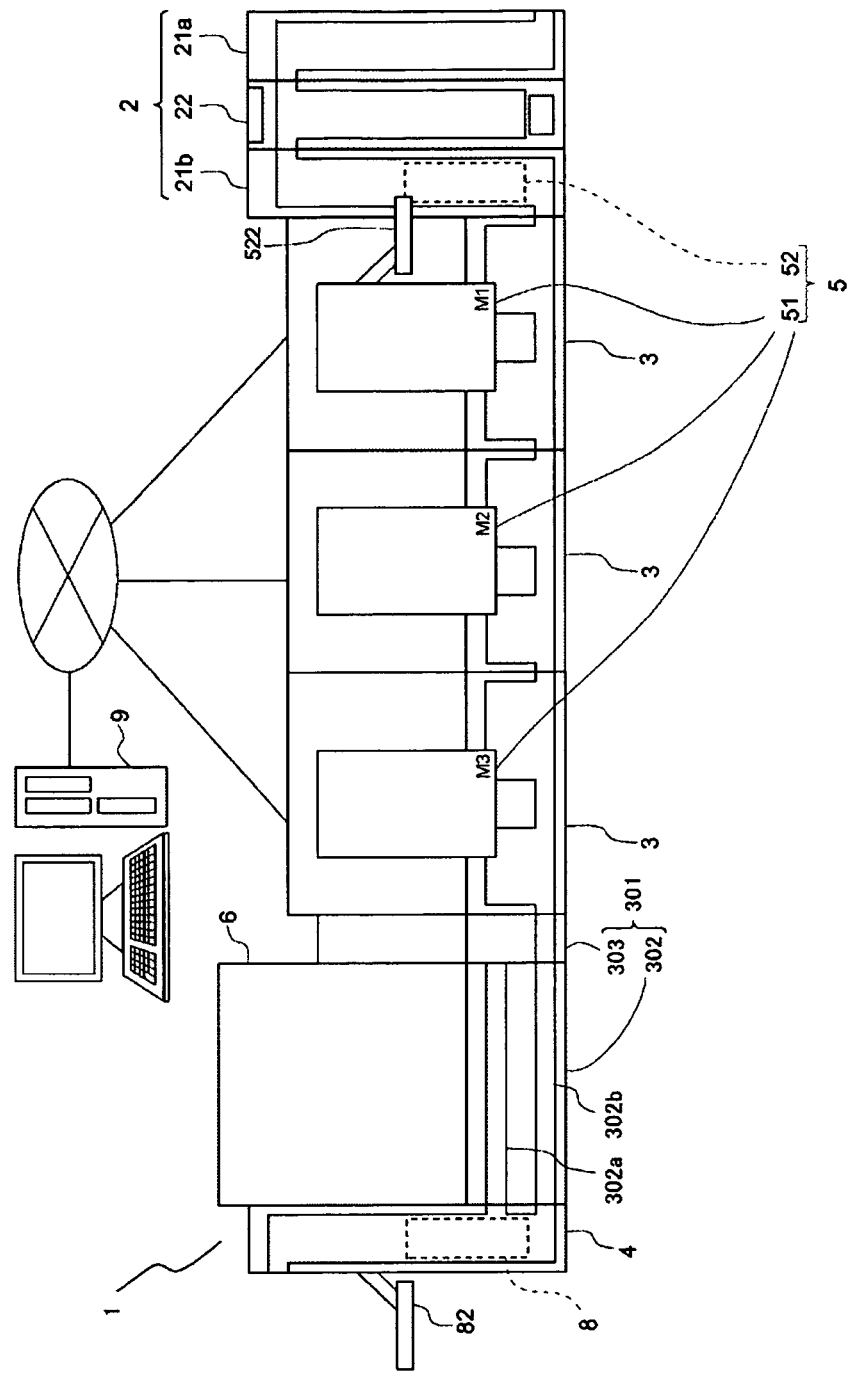
FIG. 1 is a schematic plan view showing an overall configuration of a sample processing system according to an embodiment.

FIG. 1 is a schematic plan view showing an overall configuration of the sample processing system according to the present embodiment. As shown in FIG. 1, the sample processing system 1 includes a sample inserting device 2, a sample transportation apparatuses 3, 301, a sample accommodating device 4, a blood cell analyzer 5, a smear producing device 6, and a system controller 8. The sample processing system 1 according to the present embodiment is communicably connected to a host computer 9 by way of a communication network.

<Configuration of Sample Inserting Device 2>

The sample inserting device 2 includes two sample sending units 21a, 21b, and a barcode reading unit 22 arranged between the two sample sending units 21a, 21b. The sample sending units 21a, 21b of the sample inserting device 2 are configured such that a sample rack accommodating a plurality of sample containers can be mounted. The sample rack mounted on the sample sending unit 21a is sent to the barcode reading unit 22 in order, wherein the rack ID is read from a barcode of a barcode label attached to the sample rack, and a sample ID is read from a barcode of a barcode label attached to a sample container by the barcode reading unit 22. A control unit of the sample inserting device 2 is communicably connected to the system controller 8 by way of LAN, and the read rack ID and the sample ID are transmitted to the system controller 8. The sample rack, which reading of the barcode is completed, is conveyed to the sample sending unit 21b, and sent to the sample transportation apparatus 3 from the sample sending unit 21b.

Figure 2:
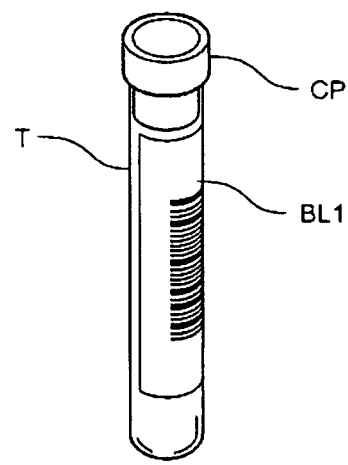
FIG. 2 is a perspective view showing an outer appearance of a sample container.
Figure 3:
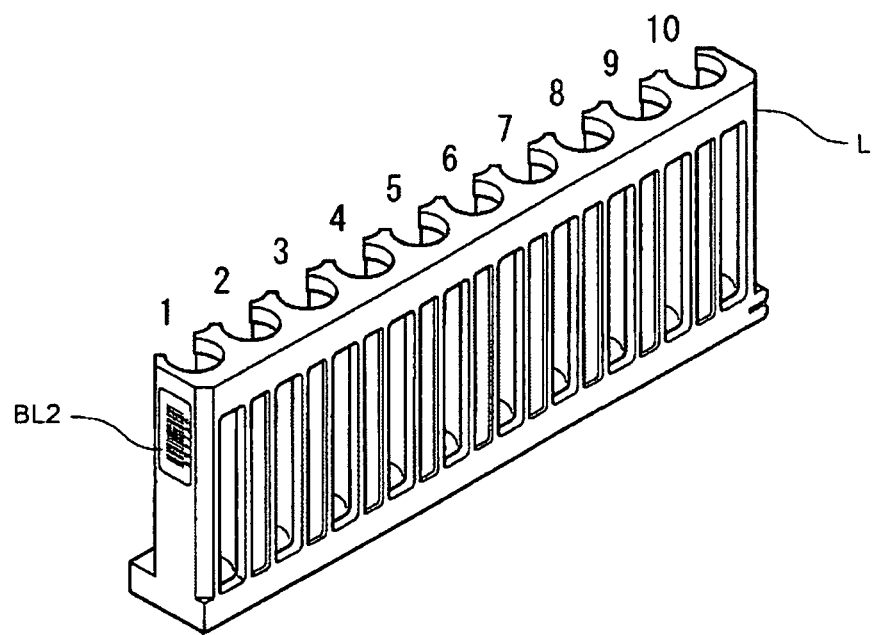
FIG. 3 is a perspective view showing an outer appearance of a sample rack.

FIG. 2 is a perspective view showing an outer appearance of a sample container, and FIG. 3 is a perspective view showing an outer appearance of a sample rack. As shown in FIG. 2, the sample container T has a tubular shape, and the upper end is opened. The blood sample collected from a patient is accommodated therein, and the opening at the upper end is sealed by a lid C. The sample container T is made of a glass or a synthetic resin having translucency, so that the blood sample inside can be seen. A barcode label BL1 is attached to the side surface of the sample container T. A barcode indicating a sample ID is printed on the barcode label BL1. The sample rack L can hold ten sample containers T side by side. Each sample container T is held in a perpendicular state (standing state) in the sample rack L. A barcode label BL2 is attached to the side surface of the sample rack L. A barcode indicating a rack ID is printed on the barcode label BL2.

<Configuration of Sample Transportation Apparatus 3>

The configuration of the sample transportation apparatus 3 will now be described. As shown in FIG. 1, the sample processing system 1 includes three sample transportation apparatuses 3. The sample transportation apparatuses 3, 3, 3 are arranged on the front side of the three measurement units 51, 51, 51 of the blood cell analyzer 5. The adjacent sample transportation apparatuses 3, 3 are connected, so that the sample rack L can be exchanged. The sample transportation apparatus 3 on the rightmost side is connected to the sample inserting device 2 described above, so that the sample rack L carried out from the sample inserting device 2 can be introduced. The sample transportation apparatus 3 on the leftmost side is connected to the sample transportation apparatus 301, so that the sample rack L can be carried out to the sample transportation apparatus 301.

Figure 4:
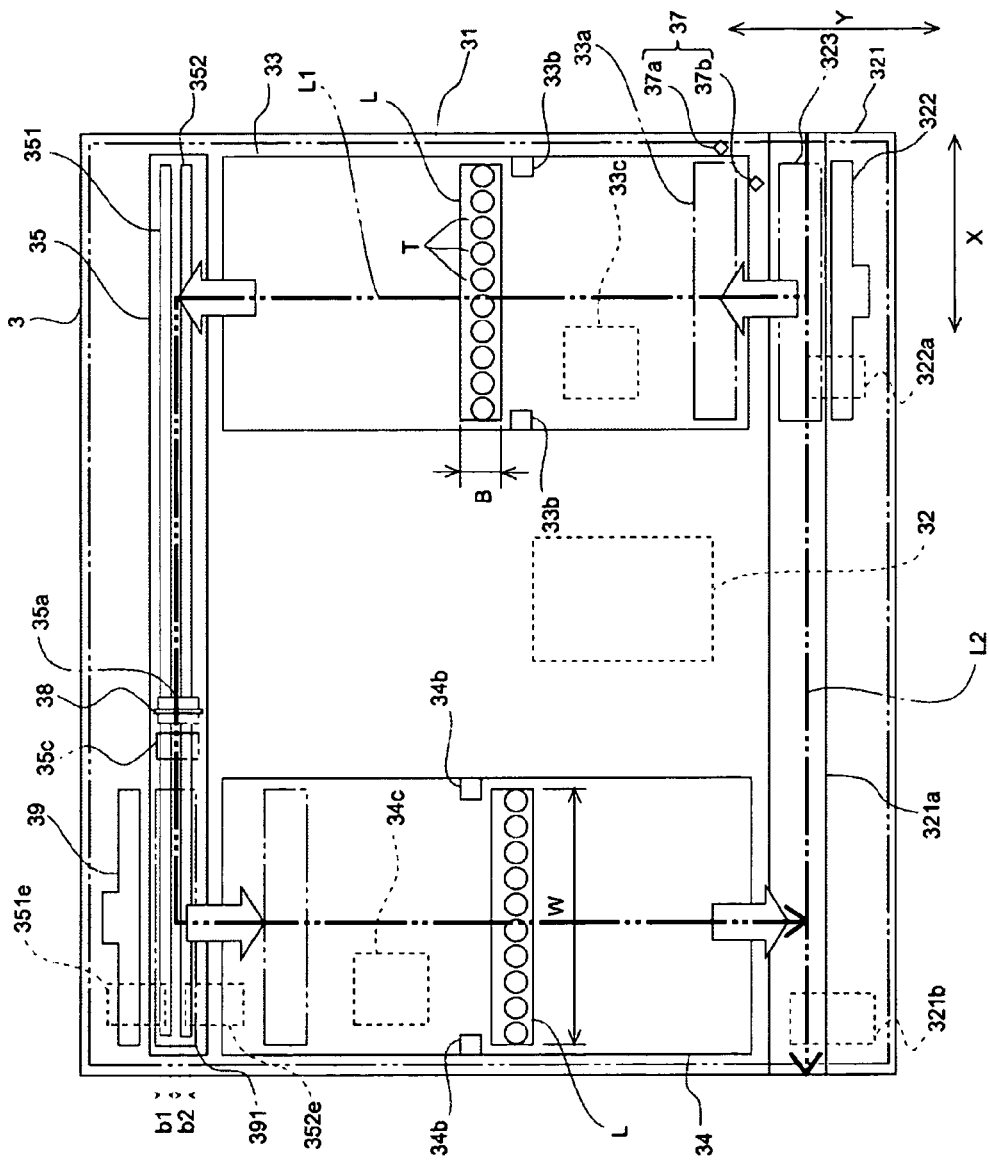
FIG. 4 is a plan view showing a configuration of a sample transportation apparatus according to an embodiment.

FIG. 4 is a plan view showing a configuration of the sample transportation apparatus 3. As shown in FIG. 4, the sample transportation apparatus 3 includes a conveyance mechanism 31 for conveying the sample and a control unit 32 for controlling the conveyance mechanism 31. The conveyance mechanism 31 includes a pre-analysis rack holder 33 capable of temporarily holding a plurality of sample racks L for holding the sample container T accommodating the sample before the analysis, a post-analysis rack holder 34 capable of temporarily holding a plurality of sample racks L for holding the sample container T from which the sample is aspirated by the measurement unit 51, a rack conveyance portion 35 for moving the sample rack L horizontally and linearly in the direction of the arrow X in the figure to supply the sample to the measurement unit 51 and conveying the sample rack L received from the pre-analysis rack holder 33 to the post-analysis rack holder 34, and a rack conveyance portion 321 for carrying in the sample rack L from the device on an upstream side of conveyance (the sample inserting device 2 or the sample transportation apparatus 3) and carrying out the sample rack L to the device on a downstream side of conveyance (the sample transportation apparatus 3 or the sample transportation apparatus 301) without supplying the sample accommodated in the sample rack L to the measurement unit 51.

The pre-analysis rack holder 33 has a square shape in plan view, which width is slightly larger than the width of the sample rack L. The pre-analysis rack holder 33 is formed to be one step lower than the peripheral surface, so that the sample rack L before the analysis is mounted on the upper surface thereof. The pre-analysis rack holder 33 is connected to the rack conveyance portion 321, so that the sample rack L is sent from the rack conveyance portion 321 by a rack sending portion 322, to be hereinafter described. A rack sensor 37 is attached near the pre-analysis rack holder 33, and a rack detection position 33a where the sample rack L is detected by the rack sensor 37 is arranged on the pre-analysis rack holder 33. The rack sensor 37 is an optical sensor, and includes a light emitting portion 37a and a light receiving portion 37b. The light emitting portion 37a is arranged on the side of the rack detection position 33a and the light receiving portion 37b is arranged on the front side of the rack detection position 33a. The light emitting portion 37a is arranged to emit light to the obliquely front side and the light receiving portion 37b is arranged to receive the light. Therefore, the sample rack L sent out from the rack conveyance portion 321 is positioned at the rack detection position 33a, wherein the light emitted from the light emitting portion 37a is blocked by the sample lack L and the received light level of the light receiving portion 37a lowers, whereby the sample rack L is detected by the sample rack 37. In other words, the rack detection position 33a is a position for temporarily waiting the sample container before being conveyed to the position where the measurement unit collects the sample from the sample container. The rack sensor 37 also detects whether or not the sample container (sample rack) exists at the relevant position. A rack send-in portion 33b is arranged projecting towards the inner side from both side surfaces of the pre-analysis rack holder 33. When the sample rack L is detected by the rack sensor 37, the rack send-in portion 33b engages with the sample rack L by projecting out, and when moved to the back side in such state (direction of approaching the rack conveyance portion 35), the sample rack L is moved to the back side. Such rack send-in portion 33b is configured to be drivable by a stepping motor 33c arranged on the lower side of the pre-analysis rack holder 33.

As shown in FIG. 4, the rack conveyance portion 35 can move the sample rack L moved by the pre-analysis rack holder 33 to the X direction. A sample container detection position 35a where the sample container is detected by a sample container sensor 38, and a sample supply position 35c where the sample is supplied to the measurement unit 51 of the blood cell analyzer 5 are provided on a conveyance path of the sample rack L by the rack conveyance portion 35. The rack conveyance portion 35 is configured to convey the sample rack L such that the sample is conveyed to the sample supply position 35c through the sample container detection position 35a. The sample supply position 35c is a position on the downstream side in the conveying direction by one sample from the sample container detection position 35a, wherein when the sample is conveyed to the sample supply position 35c by the rack conveyance portion 35, a hand portion of the measurement unit 51 of the blood cell analyzer 5, to be hereinafter described, grips the sample container T of the relevant sample, takes out the sample container T from the sample rack L, and aspirates the sample from the sample container T to supply the sample to the measurement unit 51. After conveying the sample container to the sample supply position 35c, the rack conveyance portion 35 waits for the conveyance of the sample rack L during the period until the supply of the sample is completed and the sample container T is returned to the sample rack L.

Figure 5:
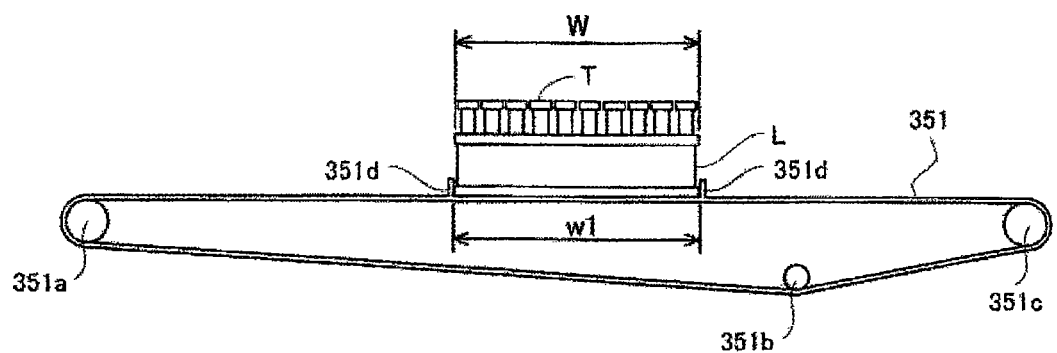
FIG. 5 is a front view showing a configuration of a first belt of the conveyance mechanism.
Figure 6:
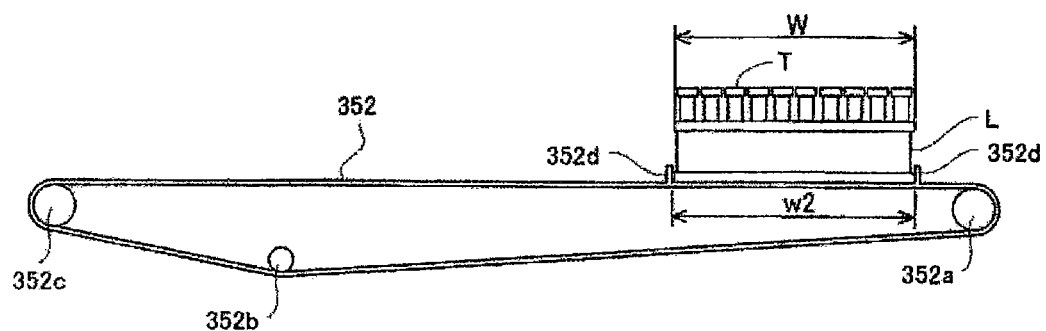
FIG. 6 is a front view showing a configuration of a second belt of the conveyance mechanism.

The rack conveyance portion 35 includes two belts, a first belt 351 and a second belt 352, that are independently operable. The widths b1 and b2 in the direction of the arrow Y of the first belt 351 and the second belt 352 are the size of smaller than or equal to half of the width B in the direction of the arrow Y of the sample rack L. Such first belt 351 and second belt 352 are arranged in parallel so as not to run out from the width B of the sample rack L when the rack conveyance portion 35 conveys the sample rack L. FIG. 5 is a front view showing a configuration of the first belt 351, and FIG. 6 is a front view showing a configuration of the second belt 352. As shown in FIGS. 5 and 6, the first belt 351 and the second belt 352 are formed to an annular shape, wherein the first belt 351 is arranged to surround rollers 351a to 351c and the second belt 352 is arranged to surround rollers 352a to 352c. Two projecting pieces 351d having an inner width w1 slightly (e.g., 1 mm) larger than the width W in the X direction of the sample rack L are arranged on the outer peripheral part of the first belt 351, and similarly, two projecting pieces 352d having an inner width w2 of the same extent as the inner width w1 are arranged on the outer peripheral part of the second belt 352. The first belt 351 is configured to move the sample rack L in the direction of the arrow X by being moved at the outer periphery of the rollers 351a to 351c by the stepping motor 351e (refer FIG. 4) while holding the sample rack L on the inner side of the two projecting pieces 351d. The second belt 352 is configured to move the sample rack L in the direction of the arrow X by being moved at the outer periphery of the rollers 352a to 352c by the stepping motor 352e (refer FIG. 4) while holding the sample rack L on the inner side of the two projecting pieces 352d. The first belt 351 and the second belt 352 are also configured to move the sample rack L independently of each other. In other words, the sample rack L can be moved to both left and right direction. Each projection piece 351d and projection 352d includes an optical sensor (not shown), and is configured to detect whether or not each projection piece is holding the sample rack L on the inner side. That is, the optical sensor detects whether or not the sample container exists at the position where the measurement unit 51 collects the sample from the sample container.

The sample container sensor 38 is a contact-type sensor, and respectively includes contact piece of store curtain shape, a light emitting element for emitting light, and a light receiving element (not shown). The sample container sensor is configured such that the contact piece is bent by contacting the detecting object of the detection target, and as a result, the light emitted from the light emitting element is reflected by the contact piece and received by the light receiving element. Therefore, when the sample container T of the detection target accommodated in the sample rack L passes below the sample container sensor 38, the contact piece is bent by the sample container T, and the sample container T is detected.

The rack sending portion 39 is arranged to face the post-analysis rack holder 34, to be hereinafter described, with the rack conveyance portion 35 in between. The rack sending portion 39 is configured to move horizontally and linearly in the direction of the arrow Y by the driving force of the stepping motor 39a. Thus, when the sample rack L is conveyed to a position 391 (hereinafter referred to as "post-analysis rack sending position") between the post-analysis rack holder 34 and the rack sending portion 39, the rack sending portion 39 is moved to the post-analysis rack holder 34 side so that the sample rack L can be pushed and moved into the post-analysis rack holder 34. The sample rack L, which analysis is completed, is sent from the rack conveyance portion 35 to the post-analysis rack holder 34 in such manner.

The rack conveyance portion 321 extends in the direction of the arrow X in the figure, and can horizontally and linearly move the sample rack L in the direction of the arrow X. Such rack conveyance portion 321 includes an annular belt 321a and a stepping motor 321b, and is configured to rotate the belt 321a in the direction of the arrow X by the driving force of the stepping motor 321b. The sample rack L mounted on the belt 321a is thereby movable in the X direction. The rack sending portion 322 is arranged to face the pre-analysis rack holder 33 with the rack conveyance portion 321 in between on the front side of the pre-analysis rack holder 33. Such rack sending portion 322 is configured to horizontally and linearly move in the direction of the arrow Y by the driving force of the stepping motor 322a. Thus, when the sample rack L is conveyed to a position 323 (hereinafter referred to as "pre-analysis rack sending position") between the pre-analysis rack holder 33 and the rack sending portion 322, the rack sending portion 322 is moved to the pre-analysis rack holder 33 side, so that sample rack L is pushed and moved to the rack detection position 33a in the pre-analysis rack holder 33.

The post-analysis rack holder 34 has a square shape in plan view, which width is slightly larger than the width of the sample rack L. The post-analysis rack holder 34 is formed to be one step lower than the peripheral surface so that the sample rack L, which analysis is completed, is mounted on the upper surface thereof. The post-analysis rack holder 34 is connected to the rack conveyance portion 35, so that the sample rack L is sent from the rack conveyance portion 35 by the rack sending portion 39. A rack send-in portion 34b is arranged projecting towards the inner side from both side surfaces of the post-analysis rack holder 34. When the sample rack L is carried in by the rack sending portion 39, the rack send-in portion 34b engages with the sample rack L by projecting out, and when moved to the front side in such state (direction of approaching the rack conveyance portion 321), the sample rack L is moved to the front side. Such rack send-in portion 34b is configured to be drivable by the stepping motor 34c arranged on the lower side of the post-analysis rack holder 34.

With such configuration, the conveyance mechanism 31 forms a measurement line L1, which is a conveyance line of the sample rack L through the sample supply position 35c, and a skip line L2, which is a conveyance line to carry out the carried-in sample rack L to the device on the downstream side without passing the sample supply position 35C.

The conveyance mechanism 31 having such configuration is controlled by the control unit 32. The control unit 32 is configured by CPU, ROM, RAM, and the like (not shown), and the CPU can execute the control program of the conveyance mechanism 31 stored in the ROM. The control unit 32 has an Ethernet (registered trademark) interface so as to be communicably connected to the information processing unit 52 and the system controller 8 through the LAN.

According to such configuration, the sample transportation apparatus 3 conveys the sample rack L conveyed from the sample inserting device 2 to the pre-analysis rack sending position 323 by the rack conveyance portion 321, moves the same to the pre-analysis rack holder 33 by the rack sending portion 322, sends the sample rack L from the pre-analysis rack holder 33 to the rack conveyance portion 35, and conveys the same by the rack conveyance portion 35, so that the sample can be supplied to the measurement unit 51 of the blood cell analyzer 5. The sample rack L accommodating the sample, which aspiration is completed, is moved to the post-analysis rack sending position 391 by the rack conveyance portion 35, and sent to the post-analysis rack holder 34 by the rack sending portion 39. The sample rack L held by the post-analysis rack holder 34 is moved to the rack conveyance portion 321, and carried out to the device of the post-stage (sample transportation apparatus 3 or 301) by the rack conveyance portion 321. If the sample rack L accommodating the sample to be processed in the measurement unit 51 or the smear producing device 6 on the downstream side of conveyance or the sample, which analysis is completed, is accepted by the sample transportation apparatus 3 from the device of the pre-stage, the sample rack L is conveyed in the direction of the arrow X by the rack conveyance portion 321, and carried out as is to the sample transportation apparatus 3 of the post-stage.

<Configuration of Sample Transportation Apparatus 301>

As shown in FIG. 1, the sample transportation apparatus 301 is arranged on the front side of the smear producing device 6. The sample transportation apparatus 301 is connected, at the right side end, to the sample transportation apparatus 3 positioned at the most downstream side of conveyance (left side in the figure) of the three sample transportation apparatuses 3, 3, 3, and is connected, at the left side end, to the sample accommodating device 4.

The sample transportation apparatus 301 includes a conveyor 302 and a rack slider 303. The conveyor 302 is arranged with two rack conveyance paths 302a, 302b respectively extending in the left and right direction. The rack conveyance path 302a proximate to the smear producing device 6 is the measurement line for conveying the sample rack L accommodating the sample to be supplied to the smear producing device 6. The rack conveyance path 302b distant from the smear producing device 6 is the skip line for conveying the sample rack L not accommodating the sample to be supplied to the smear producing device 6. The conveyor 302 includes a CPU and a memory, and includes a control unit (not shown) for controlling each operation mechanism.

The rack slider 303 is arranged on the right side of the conveyor 302, and allocates and inserts the sample rack L to the measurement line 302a and the skip line 302b of the conveyor 302.

<Configuration of Sample Accommodating Device 4>

The sample accommodating device 4 is configured so that a plurality of sample racks L can be mounted. The relevant sample accommodating device 4 receives the sample rack L, which is terminated with analysis or smear production, from the sample transportation apparatus 301, and accommodates the same.

<Configuration of Blood Cell Analyzer 5>

The blood cell analyzer 5 is a multi-item blood cell analyzer of optical flow cytometry method, and acquires the lateral scattered light intensity, the fluorescence intensity, and the like related to the blood cell contained in the blood sample, classifies the blood cell contained in the sample based on the same, counts the number of blood cells for every type, creates a scattergram in which the classified blood cells are colored by type, and displays the same. The blood cell analyzer 5 includes the measurement unit 51 for measuring the blood sample, and the information processing unit 52 for processing the measurement data output from the measurement unit 51 and displaying the analysis result of the blood sample.

As shown in FIG. 1, the blood cell analyzer 5 includes three measurement units 51, 51, 51 and one information processing unit 52. The information processing unit 52 is communicably connected to the three measurement units 51, 51, 51, and can control the operation of the three measurement units 51, 51, 51. Furthermore, the information processing unit 52 is communicably connected to the three sample transportation apparatuses 3, 3, 3, arranged respectively on the front side of the three measurement units 51, 51, 51.

Figure 7:
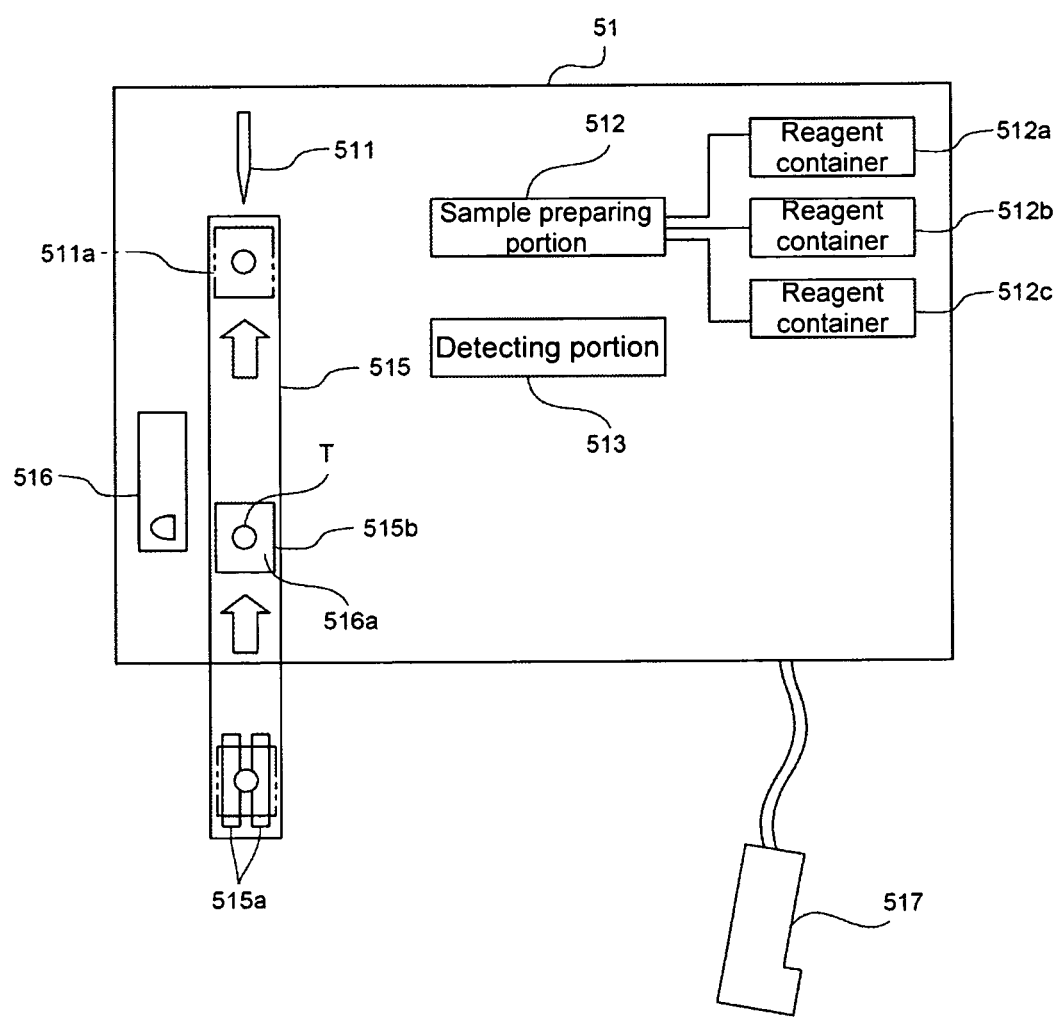
FIG. 7 is a block diagram showing a configuration of a measurement unit of a blood cell analyzer according to the embodiment.

The three measurement units 51, 51, 51 have the same configuration, and respectively measures the blood sample as an analyzer. In other words, the blood analyzer 5 is a system including three analyzers and the information processing unit. FIG. 7 is a block diagram showing a configuration of the measurement unit 51. As shown in FIG. 7, the measurement unit 51 includes a sample aspirating portion 511 for aspirating the blood or the sample from the sample container (blood collecting tube) T, a sample preparing portion 512 for preparing a measurement sample used in the measurement from the blood aspirated by the sample aspirating portion 511, and a detecting portion 513 for detecting the blood cell from the measurement sample prepared by the sample preparing portion 512. The measurement unit 51 further includes a take-in port (not shown) for taking in the sample container T accommodated in the sample rack L conveyed by the rack conveyance portion 35 of the sample transportation apparatus 3 into the measurement unit 51, and a sample container conveyance portion 515 for taking in the sample container T from the sample rack L into the measurement unit 51 and conveying the sample container T to the aspirating position by the sample aspirating portion 511.

An aspirating tube (not shown) is arranged at the distal end of the sample aspirating portion 511. The sample aspirating portion 511 is movable in the vertical direction, and is moved to the lower side so that the aspirating tube passes through the lid CP of the sample container T conveyed to the aspirating position to aspirate the blood inside.

The sample preparing portion 512 is connected to a reagent container 512a accommodating a staining reagent, a reagent container 512b accommodating a hemolyzing agent, and a reagent container 512c accommodating a diluted solution by way of a tube. The sample preparing portion 512 is connected to a compressor (not shown), so that the reagent can be dispensed from the reagent containers 512a, 512b, 512c by the pressure generated by the compressor. A barcode label is given to the reagent containers 512a, 512b, 512b, wherein information on the type of reagent (reagent name), lot number, manufactured date, and expiration date are recorded on the barcode label in a form of barcode.

The measurement unit 51 includes the reagent barcode reading portion 517. The reagent barcode reading portion 517 is a handy barcode reader, and the operator has the barcode reading portion 517 read the barcodes of the reagent containers 512a, 512b, 512c when reading the reagent barcode. The read information on the reagent type, lot number, manufactured date, and expiration date are transmitted to the information processing unit 52.

The detecting portion 513 can perform the RBC (Red Blood Cell) detection and the PLT (Platelet) detection through the sheath flow DC detection method. In the detection of the RBC and the PLT by the sheath flow DC detection method, the measurement of the measurement sample, in which the sample and the diluted solution accommodated in the reagent container 512c are mixed, is performed, wherein the information processing unit 52 performs the analyzing process on the obtained measurement data to measure the RBC and the PLT. The detecting portion 513 can perform the HGB (Hemoglobin) detection through the SLS-hemoglobin method, and is configured to perform the detection of WBC (White Blood Cell), NEUT (Neutrophil Cell), LYMPH (Lymph Cell), EO (Eosinophil), BASO (Basophil), MONO (Monocyte) and RET (Reticulocyte) through the flow cytometry method using the semiconductor laser. In the detecting portion 513, detecting methods differ for the detection of the WBC not involving five classification of the white blood cell, that is, the detection of the WBC not involving the detection of the NEUT, the LYMPH, the EO, the BASO and the MONO, and for the detection of the WBC involving five classification of the white blood cell. In the detection of the WBC not involving five classification of the white blood cell, the measurement of the measurement sample, in which the sample, the hemolyzing agent accommodated in the reagent container 512b and the diluted solution accommodated in the reagent container 512c are mixed, is performed, wherein the information processing unit 52 performs the analyzing process on the obtained measurement data to measure the WBC. On the other hand, in the detection of the WBC involving five classification of the white blood cell, the measurement of the measurement sample, in which the stain reagent accommodated in the reagent container 512a, the hemolyzing agent accommodated in the reagent container 512b and the diluted solution accommodated in the reagent container 512c are mixed, is performed, wherein the information processing unit 52 performs the analyzing process on the obtained measurement data to measure the NEUT, the LYMPH, the EO, the BASO, the MONO and the WBC. The RET can be measured together when detecting the WBC involving five classification of the white blood cell by accommodating the RET measurement stain reagent in the reagent container 512a.

The sample container conveyance portion 515 includes a hand portion 515a capable of gripping the sample container T. The hand portion 515a includes a pair of gripping members arranged facing each other, and can approach or separate the gripping members to and from each other. The sample container T can be gripped by approaching the relevant gripping members with the sample container T in between. The sample container conveyance portion 515 can move the hand portion 515a in the up and down direction and in the front and back direction (Y direction), and can oscillate the hand portion 515a. Thus, the sample container T accommodated in the sample rack L and positioned at the supply position 35c can be gripped by the hand portion 515a, the sample container T can be taken out from the sample rack L by moving the hand portion 515a upward in the relevant state, and the sample in the sample container T can be stirred by oscillating the hand portion 515a.

The sample container conveyance portion 515 includes a sample container setting portion 515b with a hole for receiving the sample container T. The sample container T gripped by the hand portion 515a described above is moved after stirring is completed, and the gripped sample container T is inserted to the hole of the sample container setting portion 515b. Thereafter, the sample container T is released from the hand portion 515a by separating the gripping members, and the sample container T is set in the sample container setting portion 515b. The relevant sample container setting portion 515b is horizontally movable in the Y direction by the power of the stepping motor (not shown). A barcode reading portion 516 is arranged inside the measurement unit 51. The sample container setting portion 515b is movable to the barcode reading position 516a near the barcode reading portion 516 and the aspirating position 511a by the sample aspirating portion 511. When the sample container setting portion 515b is moved to the barcode reading position 516a, the set sample container T is horizontally rotated by a rotation mechanism (not shown), and the sample barcode is read by the barcode reading portion 516. Thus, even if the barcode label BL1 of the sample container T is positioned on the opposite side with respect to the barcode reading portion 516, the barcode label BL1 can be directed towards the barcode reading portion 516 by rotating the sample container T so that the sample barcode can be read by the barcode reading portion 516. When the sample container setting portion 515b is moved to the aspirating position, the sample is aspirated from the set sample container T by the sample aspirating portion 511.

Figure 8:
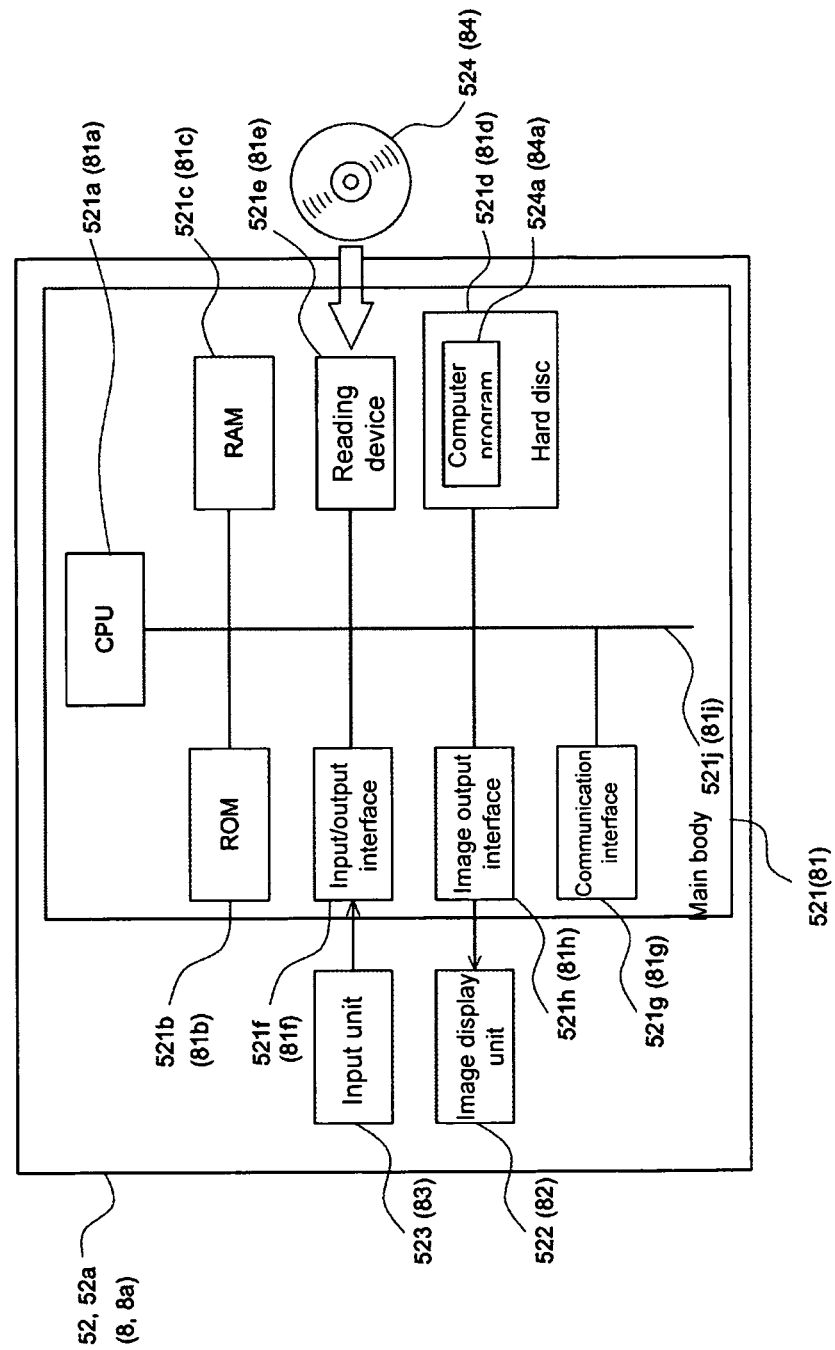
FIG. 8 is a block diagram showing a configuration of an information processing unit of the blood cell analyzer according to the embodiment.

The configuration of the information processing unit 52 will now be described. The information processing unit 52 is configured by a computer. FIG. 8 is a block diagram showing a configuration of the information processing unit 52. The information processing unit 52 is realized by a computer 52a. As shown in FIG. 8, the computer 52a includes a main body 521, an image display unit 522, and an input unit 523. The main body 521 includes a CPU 521a, a ROM 521b, a RAM 521c, a hard disc 521d, a readout device 521e, an input/output interface 521f, a communication interface 521g, and an image output interface 521h, wherein the CPU 521a, the ROM 521b, the RAM 521c, the hard disc 521d, the readout device 521e, the input/output interface 521f, the communication interface 521g, and the image output interface 521h are connected by a bus 521j.

The CPU 521a can execute the computer program loaded in the RAM 521c. The computer 52a functions as the information processing unit 52 by causing the CPU 521a to execute the computer program 524a for the sample analysis and for the control of the measurement unit 51, to be hereinafter described.

The ROM 521b is configured by mask ROM, PROM, EPROM, EEPROM, and the like, and is recorded with the computer program executed by the CPU 521a, the data used when executing the computer program, and the like.

The RAM 521c is configured by SRAM, DRAM, or the like. The RAM 521c is used to read out the computer program 524a recorded in the hard disc 521d. The RAM 521c is used as a work region of the CPU 521a when the CPU 521a executes such computer programs.

The hard disc 521d is installed with various computer programs such as an operating system and an application program to be executed by the CPU 521a, and the data used for the execution of the computer program. The computer program 524a to be hereinafter described is also installed in the hard disc 521d.

The readout device 521e is configured by flexible disc drive, CD-ROM drive, DVD-ROM drive, or the like. The readout device 521e can read out computer program or data recorded in a portable recording medium 524. The portable recording medium 524 stores the application program 524a for causing the computer to function as the information processing unit 52, wherein the computer 52a reads out the computer program 524a from the portable recording medium 524, and installs the computer program 524a in the hard disc 521d.

The computer program 524a is not limited to being provided by the portable recording medium 524, and may be provided through an electrical communication line from an external device communicably connected to the computer 52a by the electrical communication line (wired or wireless). For instance, the computer program 524a may be stored in a hard disc of a server computer on the Internet, and the computer 52a may access the server computer, download the computer program, and store the same in the hard disc 521d.

The hard disc 521d is installed with a multi-task operating system such as Windows (registered trademark) manufactured and sold by US Microsoft Co. In the following description, the computer program 524a according to the present embodiment operates on the operating system.

The input/output interface 521f is configured by serial interface such as USB, IEEE1394, RS-232C; parallel interface such as SCSI, IDE, IEEE1284; analog interface including D/A converter, A/D converter and the like. The input/output interface 521f is connected with the input unit 523 such as a keyboard and a mouse, and the user can input data to the computer 52a by using the input unit 523. The input/output interface 521f is connected to three measurement units 51, 51, 51. The data can be transmitted and received among each of the three measurement units 51, 51, 51.

The communication interface 521g is an Ethernet (registered trademark) interface. The communication interface 521g is connected to the system controller 8 through the LAN. The computer 52a can transmit and receive data with the system controller 8 connected to the LAN by using a predetermined communication protocol by the communication interface 521g. The communication interface 521g is communicably connected to the host computer 9 and each sample transportation apparatus 3, 3, 3 through the LAN.

The image output interface 521h is connected to the image display unit 522 configured by LCD, CRT, or the like, and outputs a video signal corresponding to the image data provided from the CPU 521a to the image display unit 522. The image display unit 522 displays an image (screen) according to the input video signal.

<Configuration of Smear Producing Device 6>

The smear producing device 6 aspirates the blood sample, drops the blood sample on a slide glass, thinly spreads the blood sample on the slide glass, dries the blood sample, and then supplies staining fluid to the slide glass to stain the blood on the slide glass to thereby produce the smear.

Figures 9, 10:
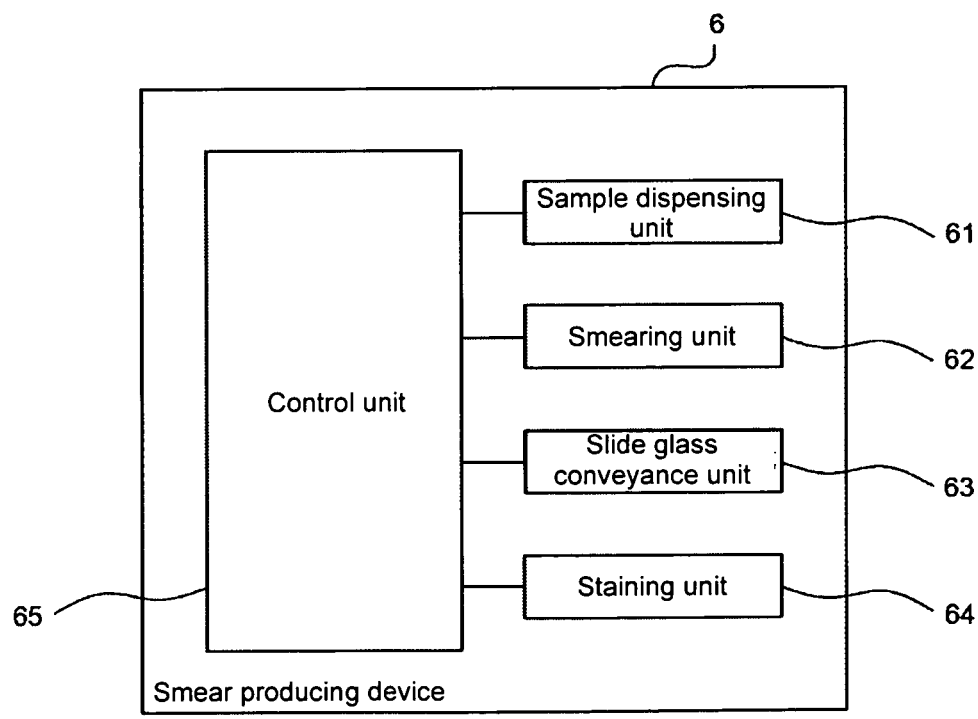
FIG. 9 is a schematic view showing a structure of a measurement unit management table.
FIG. 10 is a block diagram showing a schematic configuration of a smear producing device according to the embodiment.

FIG. 10 is a block diagram showing a schematic configuration of the smear producing device 6. As shown in FIG. 10, the smear producing device 6 includes a sample dispensing unit 61, a smearing unit 62, a slide glass conveyance unit 63, a staining unit 64, and a control unit 65.

The sample dispensing unit 61 includes an aspiration tube (not shown), which aspiration tube is pierced to the lid C of the sample container T of the sample rack L conveyed on the measurement line 31a of the sample transportation apparatus 3 to aspirate the blood sample from the sample container T. The sample dispensing unit 61 is configured to drop the aspirated blood sample on the slide glass. The smearing unit 62 is configured to smear and dry the blood sample dropped onto the slide glass, and to print on the slide glass.

The slide glass conveyance unit 63 is provided to accommodate the slide glass smeared with the blood sample by the smearing unit 62 in the cassette (not shown) and further convey such cassette. The staining unit 64 supplies the staining fluid to the slide glass in the cassette conveyed to the staining position by the slide glass conveyance unit 63. The control unit 65 controls the sample dispensing unit 61, the smearing unit 62, the slide glass conveyance unit 63, and the staining unit 64 according to a sample producing instruction provided from the sample transportation apparatus 3 to execute the smear producing operation.

<Configuration of System Controller 8>

The system controller 8 is configured by a computer, and controls the entire sample processing system 1. The system controller 8 accepts the number of the sample rack L from the sample inserting device 2, and determines the conveying destination of the sample rack L.

The system controller 8 is configured by a computer 8a. As shown in FIG. 8, the computer 8a includes a main body 81, an image display unit 82, and an input unit 83. The main body 81 includes a CPU 81a, a ROM 81b, a RAM 81c, a hard disc 81d, a readout device 81e, an input/output interface 81f, a communication interface 81g, and an image output interface 81h, wherein the CPU 81a, the ROM 81b, the RAM 81c, the hard disc 81d, the readout device 81e, the input/output interface 81f, the communication interface 81g, and the image output interface 81h are connected by a bus 81j.

The hard disc 81d is installed with various computer programs such as an operating system and an application program to be executed by the CPU 81a, and the data used for the execution of the computer program. The system control program 84a to be hereinafter described is also installed in the hard disc 81d.

The hard disc 81d includes a measurement unit management table TBL. FIG. 9 is a schematic view showing a structure of the measurement unit management table TBL. The measurement unit management table TBL is data for performing management of the application assigned to each measurement unit. Each measurement unit is used for the primary measurement or for the primary measurement and the review measurement. The application assigned to every measurement unit is registered in the measurement unit management table TBL. In the table, the measurement unit ID is information used to distinguish the three measurement units 51, 51, 51. Each measurement unit 51 is assigned a unique measurement unit ID. The measurement ID of "M1", "M2", and "M3" are assigned to the measurement units 51, 51, 51 in the present embodiment in the order from the upstream side to the downstream side of conveyance.

The measurement unit management table TBL includes a field F1 indicating the measurement unit ID, a field F2 indicating whether or not the measurement unit is for the primary measurement, and a field F3 indicating whether or not the measurement unit is for the review measurement. The flag of "0" or "1" is set for the field F2 and the field F3. If the flag is "1" in the field F2, this means that the measurement unit is used for the primary measurement, and if the flag is "0", this means that the measurement unit is not used for the primary measurement. If the flag is "1" in the field F3, this means that the measurement unit is used for the review measurement, and if the flag is "0", this means that the measurement unit is not used for the review measurement. In the example shown in FIG. 9, both measurement units M1 and M2 are set and registered to be dedicated for the primary measurement, and the measurement unit M3 is set and registered to perform the review measurement in addition to the primary measurement. In the present embodiment, each measurement item of RBC, PLT, WBC, NEUT, LYMP, EO, BASO, and MONO is measured in the primary measurement in all of the measurement units M1, M2 and M3. Therefore, the measurement units M1, M2, and M3 perform the measurement of the common measurement items for the primary measurement. In the review measurement in the measurement unit M3, the RET is measured in addition to each measurement item above. Therefore, only the measurement unit M3 includes the RET measurement stain reagent specific for the review measurement.

The readout device 81e is configured by flexible disc drive, CD-ROM drive, DVD-ROM drive, or the like, and can read out computer program or data recorded in a portable recording medium 84. The portable recording medium 84 stores the system control program 84a for causing the computer to function as the system controller 8, wherein the computer 8a reads out the system control program 84a from the portable recording medium 84, and installs the system control program 84a in the hard disc 81d.

The input/output interface 81f is configured by serial interface such as USB, IEEE1394, RS-232C; parallel interface such as SCSI, IDE, IEEE1284; analog interface including D/A converter, A/D converter and the like. The input/output interface 81f is connected with the input unit 83 such as a keyboard and a mouse, and the user can input data to the computer 52a by using the input unit 83.

The communication interface 81g is an Ethernet (registered trademark) interface. The communication interface 81g is connected to the sample inserting device 2, the sample transportation apparatus 3, the sample accommodating device 4, the information processing unit 52, and the host computer 9 through the LAN. The computer 8a can transmit and receive data with each device connected to the LAN by using a predetermined communication protocol by the communication interface 81g.

Other configurations of the system controller 8 are similar to the configuration of the information processing unit 52, and thus the description thereof will be omitted.

<Configuration of Host Computer 9>

The host computer 9 is configured by a computer and includes a CPU, a ROM, a RAM, a hard disc, a communication interface, and the like. The communication interface is connected to the LAN to communicate with the system controller 8, the information processing unit 52 of the blood cell analyzer 5, the sample inserting device 2, the sample transportation apparatus 3, and the sample accommodating device 4. The hard disc stores measurement orders. The measurement order contains information of the sample ID and the measurement item to be conducted. When receiving request data of the measurement order containing the sample ID from another device, the host computer 9 reads out the measurement order corresponding to the sample ID from the hard disc, and transmits to the device of the requesting source. Other configurations of the host computer 9 are similar to the configuration of other computers described above, and thus the description thereof will be omitted.

The operation of the sample processing system 1 according to the present embodiment will be described below.

[Measurement Unit Application Registering Operation]

The measurement unit application registering operation of the sample processing system 1 will be described. In the sample processing system 1, each measurement unit 51, 51, 51 is used for the primary measurement, or for the primary measurement and for the review measurement. The application assigned for every measurement unit is registered in the measurement unit management table TBL. The registration of measurement unit application is performed by the system controller 8.

FIG. 11 is a flowchart showing a procedure of a displaying process of a measurement unit application registration screen of the system controller 8. The operator or the service man operates the input unit 83 of the system controller 8 to input a displaying instruction of the measurement unit application registration screen when registering the measurement unit application. The displaying instruction of the measurement unit application registration screen is provided to the CPU 81a (step S201). The computer program 84a executed by the CPU 81a of the system controller 8 is an event-driven type program, wherein the process of step S202 is called out when an event of accepting the displaying instruction of a conveyance mode setting screen occurs in the CPU 81a.

Figure 14:
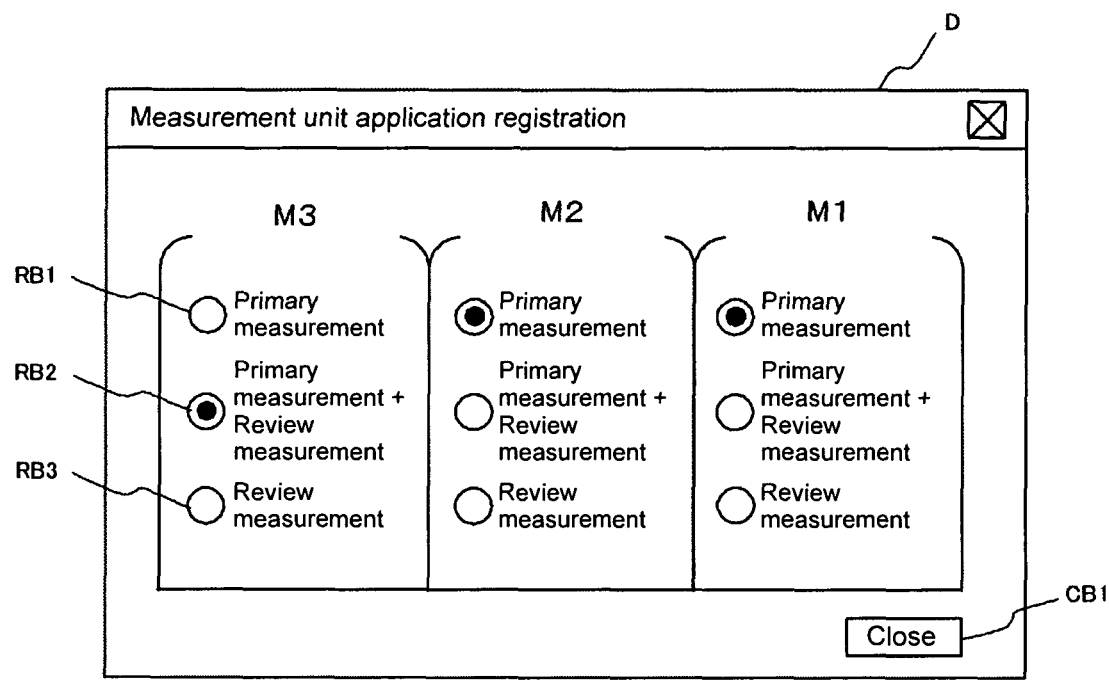
FIG. 14 is a view showing the measurement unit application registration screen of the system controller.

In step S202, the CPU 81a causes the image display unit 82 to display the measurement unit application registration screen (step S202), and terminates the process. FIG. 14 is a view showing a measurement unit application registration screen. As shown in the figure, the measurement unit application registration screen D includes, for every measurement unit M1, M2, M3, radio buttons RB1 to RB3 for selecting the application (for primary measurement, for primary measurement and review measurement, or for review measurement). The radio buttons RB1 to RB3 can be selected by the operator or the service man by performing a predetermined operation (e.g., click left button of mouse) on the input unit 83. When the radio button RB1 of each measurement unit is selected, the application of the corresponding measurement unit is registered as for the primary measurement. When the RB2 is selected, the application of the corresponding measurement unit is registered as for the primary measurement and for the review measurement. When the RB3 is selected, the application of the corresponding measurement unit is registered as for the review measurement. As shown in the figure, the measurement unit application registration screen D also includes a selectable close button CB1 for accepting an instruction to terminate the display of the measurement unit application registration screen D.

FIG. 12 is a flowchart showing a procedure of the measurement unit application registration process in the measurement unit application registration screen. The operator or the service man selects the radio button of the desired application in each measurement unit from the radio buttons RB1 to RB3 while the measurement unit application registration screen D is displayed, and a setting and registering instruction of the application (for primary measurement, for primary measurement and review measurement, or for review measurement) for every measurement unit by the selection of the radio button is provided to the CPU 81b (step S211). When an event of accepting the selection of one of the radio buttons RB1 to RB3 occurs, the CPU 81a sets the selected application for each measurement unit (step S212). This process is performed by setting the measurement unit application flag of the measurement unit management table TBL arranged in the hard disc 81d. That is, when the radio button RB1 is selected, the primary measurement flag of the field F2 of the corresponding measurement unit is set to "1", and the review measurement flag of the field F3 is set to "0". When the radio button RB2 is selected, the primary measurement flag of the field F2 of the corresponding measurement unit is set to "1", and the review measurement flag of the field F3 is also set to "1". When the radio button R3 is selected, the primary measurement flag of the field F2 of the corresponding measurement unit is set to "0", and the review measurement flag of the field F3 is set to "1". The CPU 81b then terminates the process.

Figure 13:
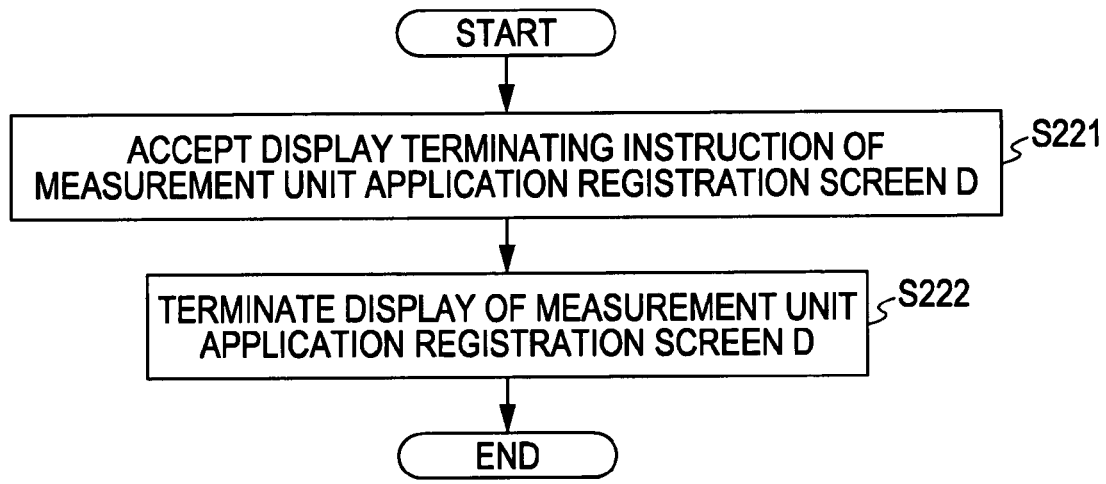
FIG. 13 is a flowchart showing a procedure of the display terminating process of the measurement unit application registration screen of the system controller.

FIG. 13 is a flowchart showing a flow of the display terminating process of the measurement unit application registration screen. The operator or the service man selects the close button B1 when the registration of the measurement unit application is terminated. When an event of accepting the selection of the close button B1 occurs (step S221), the CPU 81a terminates the display of the measurement unit application registration screen D (step S222), and terminates the process.

[Sample Conveying Operation]
<Operation of Sample Inserting Device 2>

An operator mounts the sample rack L accommodating the sample container T on the sample sending unit 21*a*, operates the operation panel (not shown) of the sample sending unit 21*a*, and gives an instruction to start the analysis to the sample analyzing system 1. The control unit of the sample sending unit 21*a* accepts such instruction to start the analysis, and starts to move the sample rack L. The sample rack L mounted on the sample sending unit 21*a* is moved to the back side on the sample sending unit 21*a*, and then the sample rack L is moved to the left direction and transferred to the barcode reading unit 22.

The sample rack L introduced to the barcode reading unit 22 is moved in the left direction by one pitch on the conveyance path by the control unit of the barcode reading unit 22. The rack barcode of the sample rack L and the sample barcode of the sample container T are read by the barcode reader. The sample rack is further moved in the left direction, and such sample rack L is moved to the sample sending unit 21*a*. The control unit of the sample sending unit 21*b* moves the received sample rack L. Thereafter, the sample inserting device 2 transmits carry-out request data including the read rack ID and the sample ID to the system controller 8, and waits for carry-out instruction data to be transmitted from the system controller 8. When receiving the carry-out instruction data from the system controller 8, the sample inserting device 2 carries out the sample rack L out to the adjacent sample transportation apparatus 3, and transmits the carry-out completion data to the system controller 8.

<Operation of System Controller 8>

The operation of the system controller 8 will be described below. When performing the primary measurement on the sample held by the sample inserting device 2, the system controller 8 receives the carry-out request data from the sample inserting device 2 and determines the conveying destination of the sample rack L by using the sample ID contained in the carry-out request data. This operation will be specifically described below.

Figure 15:
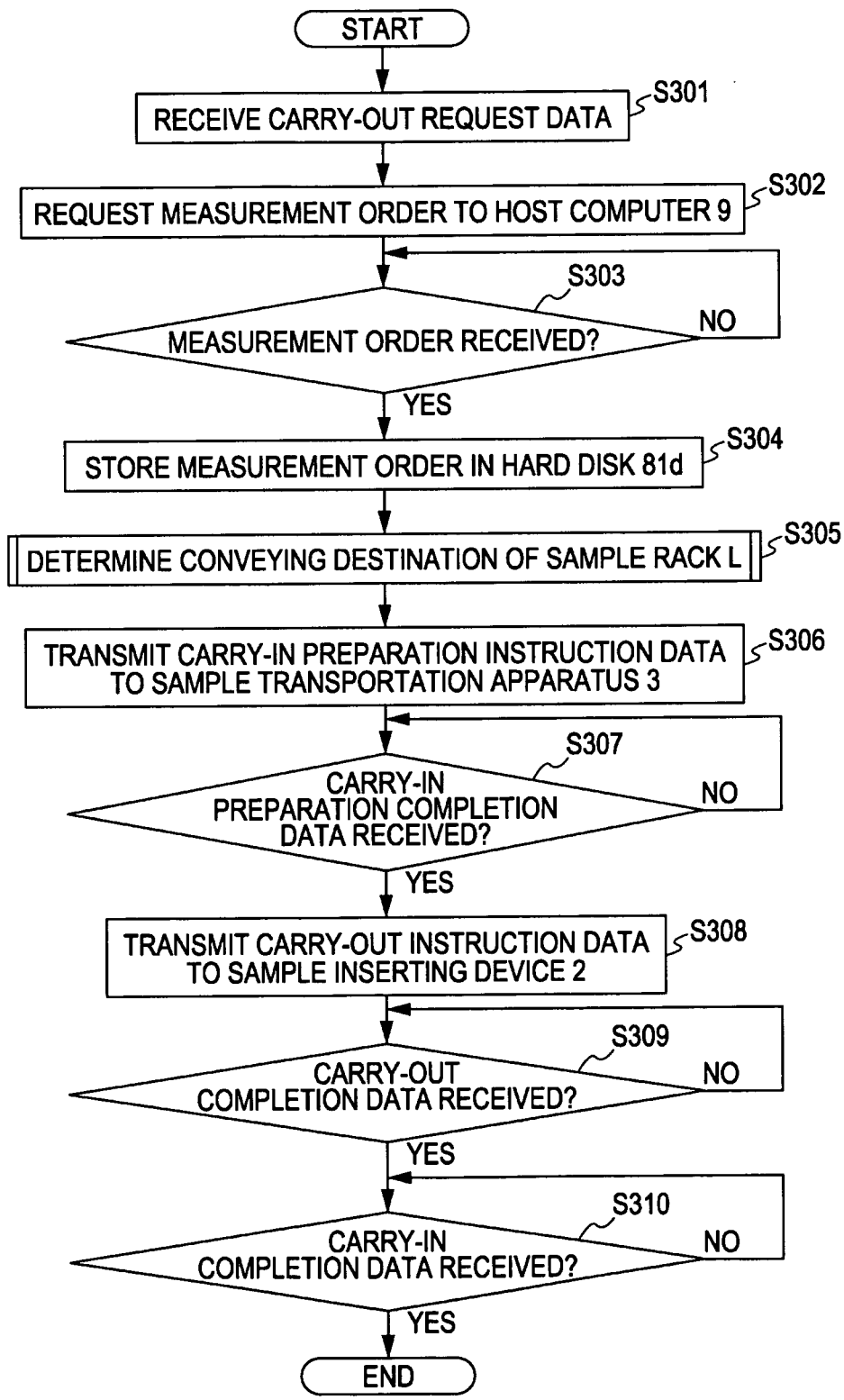
FIG. 15 is a flowchart showing a procedure of a first conveyance instruction process of the system controller.

FIG. 15 is a flowchart showing a procedure of a first conveyance instruction process of the system controller 8. In the first conveyance instruction process, the conveying destination of the sample rack L is determined, and the conveyance instruction is provided to the sample transportation apparatus 3 arranged on the front side of the M1 measurement unit 51. The carry-out request data transmitted from the sample inserting device 2 is received by the communication interface 81*g* of the system controller 8 (step S301). The process of step S302 is called out when the event of receiving the carry-out request data occurs in the CPU 81*a*.

In step S302, the CPU 81*a* transmits all sample ID contained in the received carry-out request data and requests for the measurement order corresponding to the sample ID to the host computer 9 (step S302). The CPU 81*a* waits for the reception of the measurement order (NO in step S303), and when receiving the measurement order transmitted from the host computer 9 by the system controller 8 (YES in step S303), stores the received measurement order in the hard disc 81*d* in correspondence to the rack ID (step S304). The received measurement order is the order of the primary measurement, and thus the system control unit recognizes that the sample to be conveyed is the target of the primary measurement. The CPU 81*a* then determines the conveying destination of the sample rack L (step S305).

Figure 16:
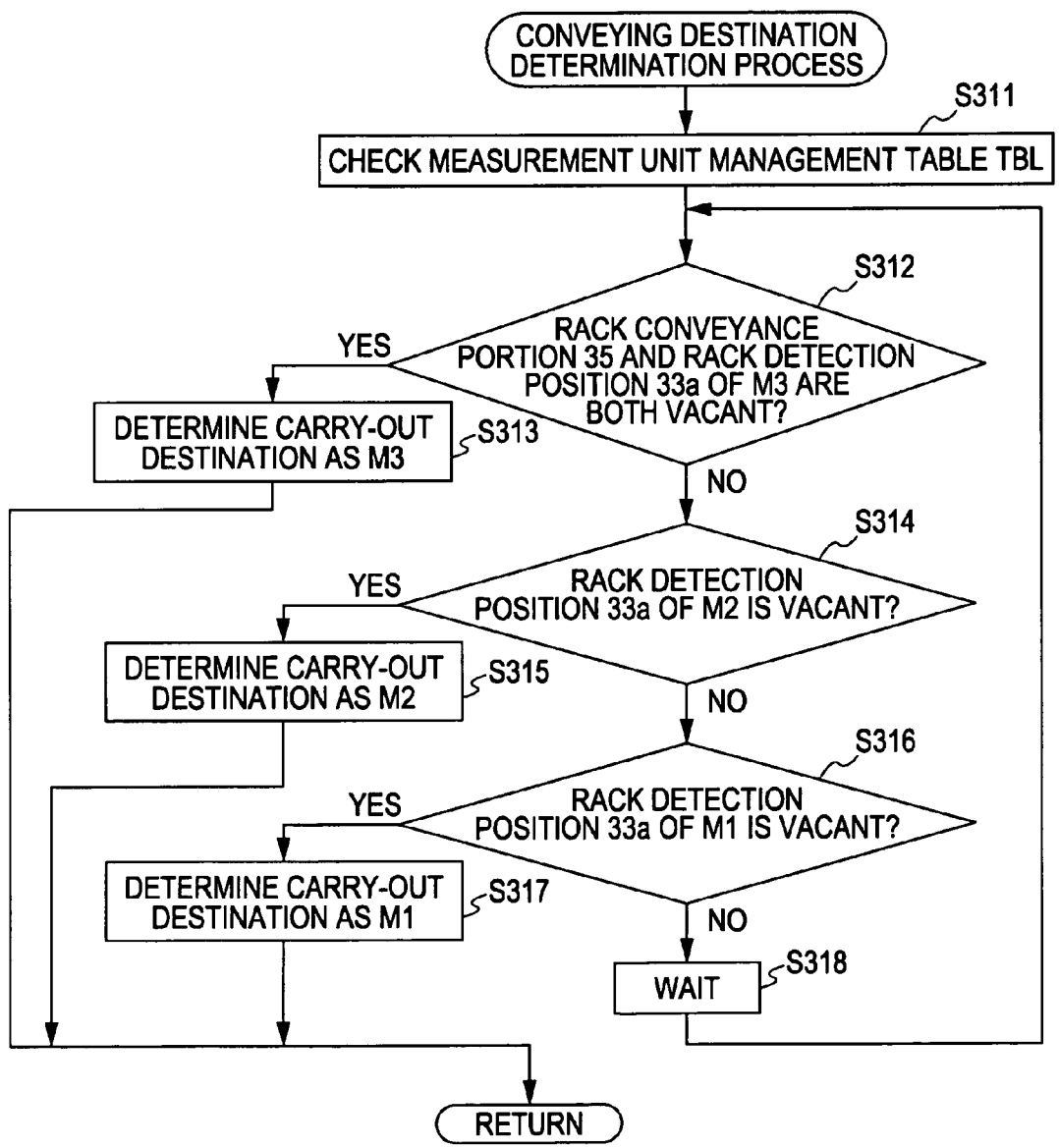
FIG. 16 is a flowchart showing a procedure of the conveying destination determining process.

The conveying destination determining process of step S305 will now be described. FIG. 16 is a flowchart showing a procedure of the conveying destination determining process. The CPU 81*a* first reads out the measurement unit application flag of the measurement unit management table TBL, and checks the current registration status. Both the measurement units M1 and M2 are registered only for primary measurement, and the measurement unit M3 on the most downstream of the conveying direction is registered for the primary measurement and the review measurement (step S311).

The CPU 81*a* determines the presence of the sample rack at the rack conveyance portion 35 and the rack detection position 33*a* of the sample transportation apparatus 3 corresponding to the measurement unit M3 on the most downstream in the conveying direction (step S312). If the sample rack does not exist in the rack conveyance portion 35 and the rack detection position 33*a* (YES in step S312), the conveying destination of the sample rack L to be conveyed is determined as the measurement unit M3 (step S313). If determined that the sample rack exists in one of or both of the rack conveyance portion 35 and the rack detection position 33*a* (NO in step S312), the CPU 81*a* determines the presence of the sample rack at the rack detection position 33*a* of the sample transportation apparatus 3 corresponding to the measurement unit M2 at the downstream in the conveying direction after the measurement unit M3 (step S314). If the sample rack does not exist at the rack detection position 33*a* (YES in step S314), the conveying destination of the sample rack L to be conveyed is determined as the measurement unit M2 (step S315). If determined that the sample rack exists at the rack detection position 33*a* (NO in step S314), the CPU 81*a* determines the presence of the sample rack at the rack detection position 33*a* of the sample transportation apparatus 3 corresponding to the measurement unit M1 on the most upstream in the conveying direction (step S316). If the sample rack does not exist at the rack detection position 33*a* (YES in step S316), the conveying destination of the sample rack L to be conveyed is determined as the measurement unit M1 (step S317). If determined that the sample rack exists at the rack detection position 33*a* (NO in step S316), an appropriate measurement unit does not currently exist for the conveying destination, and thus waits for a predetermined time (step S318), and the process thereafter returns to step S312, and the steps after S312 are repeated.

When performing the determination of the presence of the sample rack at the rack conveyance portion 35 or the rack detection position 33*a* of the analyzing unit M1, M2, or M3 in steps S312, S314, and S316, the CPU 81*a* inquires the control unit 32 of the sample transportation apparatus 3 and determines the presence of the sample rack at each position. The control unit 32 of the sample transportation apparatus 3 detects the presence of the sample rack at the rack conveyance portion 35 by an optical sensor of the projection piece 351*d* of the first belt 351 and the projection piece 352*d* of the second belt 352. The control unit 32 of the sample transportation apparatus 3 detects the presence of the sample rack at the rack detection position 33*a* by the rack sensor 37 arranged near the pre-analysis rack holder.

According to such configuration, the sample of the primary measurement is conveyed to the measurement unit M3 for performing both the primary measurement and the review measurement only if the sample currently being measured does not exist and the sample waiting to be measured does not exist (YES in step S312). The sample to be the target of the primary measurement is not conveyed if the sample being measured or the sample being waited exists in the measurement unit M3. Therefore, the sample or the target of the primary measurement concentrates on the measurement unit M3, which is the only one used for the review measurement of the measurement units M1, M2, and M3, and a state where the sample or the target of review measurement cannot be measured can be avoided. As the sample is preferentially conveyed to the measurement unit on the downstream side in the conveying direction, in principle, the sample of after the measurement can be rapidly conveyed to the sample accommodating device 4, and the series of measurement processes can be rapidly completed.

The CPU 81a transmits carry-in preparation instruction data of the sample rack L based on the determined conveying destination to the sample transportation apparatus 3 adjacent to the sample inserting device 2 (i.e., sample transportation apparatus 3 on the most right side in FIG. 1) (step S306). The carry-in preparation instruction data contains data (hereinafter referred to as "use conveyance line instruction data") indicating the conveyance line (measurement line L1 or skip line L2) for conveying the sample rack L in such sample transportation apparatus 3, and the measurement order of each sample of the sample rack L. That is, if the conveying destination of the sample rack L is the M1 measurement unit 51, data indicating the measurement line L1 is set as the use conveyance line instruction data in the carry-in preparation instruction data. If the M2 or M3 measurement unit 51 is determined as the conveying destination, data indicating the skip line L2 is set as the use conveyance line instruction data in the carry-in preparation instruction data. The sample transportation apparatus 3 receiving the carry-in preparation instruction data executes the preparation operation (operation enabling the reception of the sample rack L) of the conveyance mechanism indicated by the use conveyance line instruction data contained in the carry-in preparation instruction data, and then transmits the carry-in preparation completion data.

The CPU 81a waits for the carry-in preparation completion data from the sample transportation apparatus 3 (NO in step S307). The carry-in preparation completion data is transmitted from the sample transportation apparatus 3, when the system controller 8 receives the carry-in preparation completion data (YES in step S307), the CPU 81a transmits the carry-out instruction data of the sample rack L to the sample inserting device 2 (Step S308). As described above, when receiving the carry-out instruction data, the sample inserting device 2 carries out the sample rack L to the sample transportation apparatus 3 and transmits the carry-out completion data. The CPU 81a waits for the carry-out completion data from the sample inserting device 2 (NO in step S309). The carry-out completion data is transmitted from the sample inserting device 2, when the system controller 8 receives the carry-out completion data (YES in step S309), the CPU 81a waists for the carry-in completion data from the sample transportation apparatus 3 (NO in step S310). The carry-in completion data is transmitted from the sample transportation apparatus 3, when the system controller 8 receives the carry-in completion data (YES in step S310), the CPU 81a terminates the process.

Figure 17:
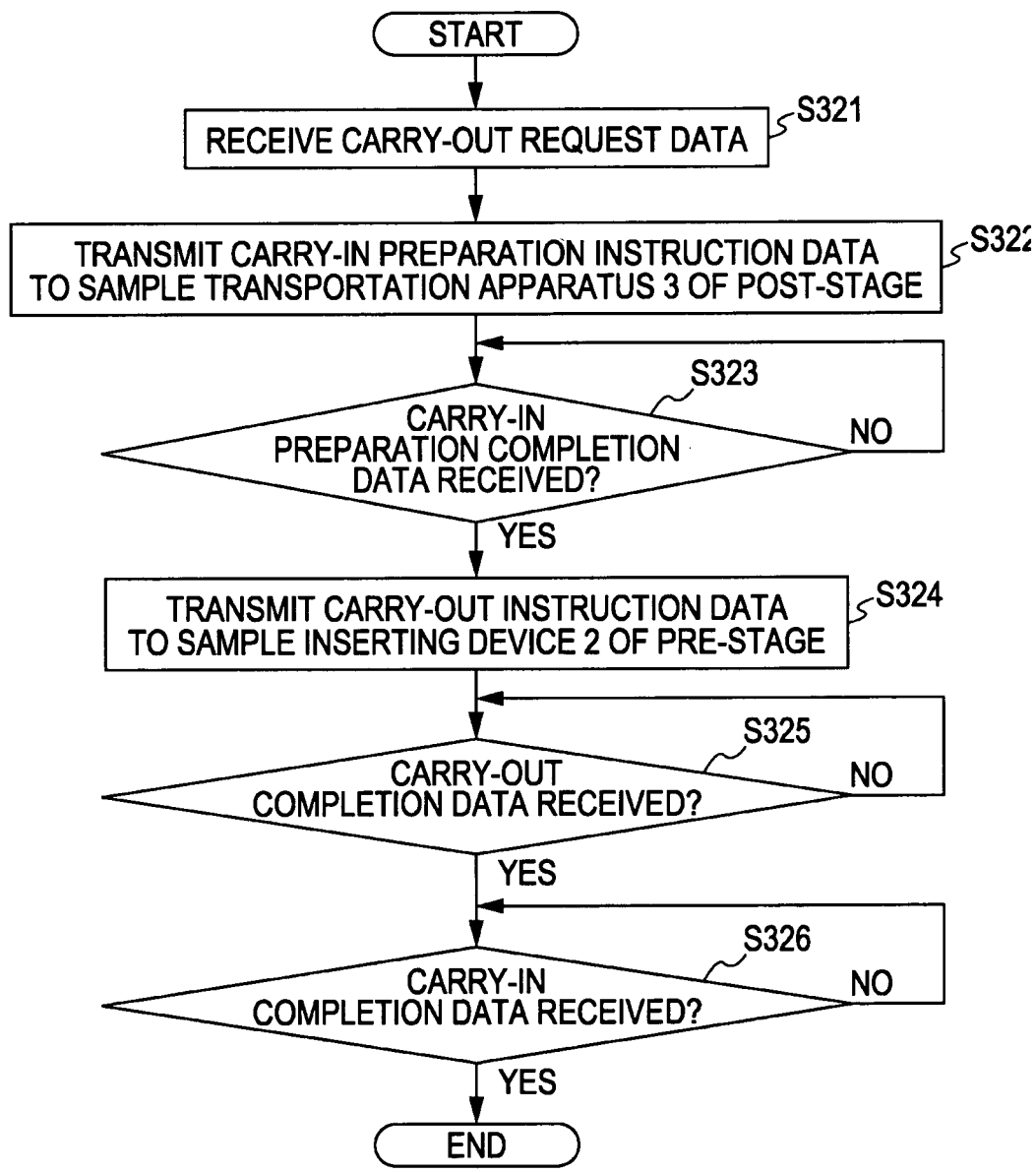
FIG. 17 is a flowchart showing a procedure of a second conveyance instruction process of the system controller.

The second conveyance instruction process of the system controller 8 will be described below. In the second conveyance instruction process, the conveyance instruction is provided to the sample transportation apparatus 3 arranged on the front side of the M2 or M3 measurement unit 51. FIG. 17 is a flowchart showing a procedure of a second conveyance instruction process. The sample rack L is conveyed by the sample transportation apparatus 3, when the sample rack L reaches the carry-out position for carrying out the sample rack L to the sample transportation apparatus 3 (or sample transportation apparatus 3) of post-stage, the carry-out request data including the rack ID of the sample rack L is transmitted from the sample transportation apparatus 3. The carry-out request data transmitted from the sample transportation apparatus 3 is received by the communication interface 81g of the system controller 8 (step S321). In the CPU 81a, the process of step S322 is called out when an event of receiving the carry-out request data from the sample transportation apparatus 3 occurs.

In step S322, the CPU 81a transmits the carry-in preparation instruction data of the sample rack L based on the conveying destination determined in the conveying destination determination process to the sample transportation apparatus 3 of the post-stage of the relevant sample transportation apparatus 3 (step S322). The carry-in preparation instruction data is similar to the carry-in preparation instruction data described above, and thus the description thereof will be omitted.

The CPU 81a waits for the carry-in preparation completion data from the sample transportation apparatus 3 (NO in step S323). The carry-in preparation completion data is transmitted from the sample transportation apparatus 3, when the system controller 8 receives the carry-in preparation completion data (YES in step S323), the CPU 81a transmits the carry-out instruction data of the sample rack L to the sample transportation apparatus 3 on the pre-stage (carry-out side) (step S324). When receiving the carry-out instruction data, the sample transportation apparatus 3 of the pre-stage carries out the sample rack L to the sample transportation apparatus 3 of the post-stage, and transmits the carry-out completion data. The CPU 81a waits for the carry-out completion data from the sample transportation apparatus 3 of the pre-stage (NO in step S325) and the carry-out completion data is transmitted from the sample transportation apparatus 3 of the pre-stage, when the system controller 8 receives the carry-out completion data (YES in step S325), the CPU 81a waits for the carry-in completion data from the sample transportation apparatus 3 of the post-stage (NO in step S326). When the carry-in completion data is transmitted from the sample transportation apparatus 3 of the post-stage, and the system controller 8 receives such carry-in completion data (YES in step S326), the CPU 81a terminates the process.

<Review Measurement Processing Operation in System Controller 8>

Figure 18:
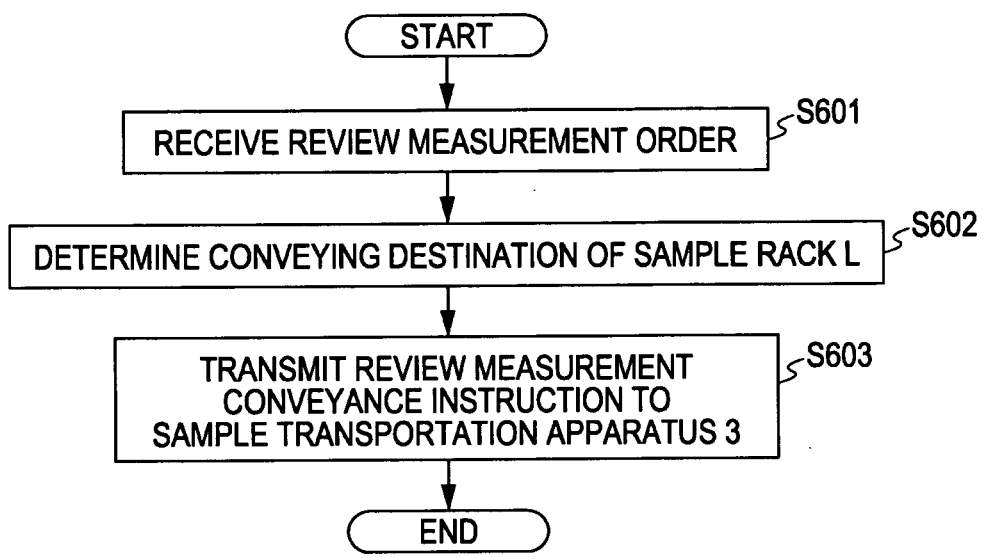
FIG. 18 is a flowchart showing a procedure of a review measurement process of the system controller.
Figure 19:
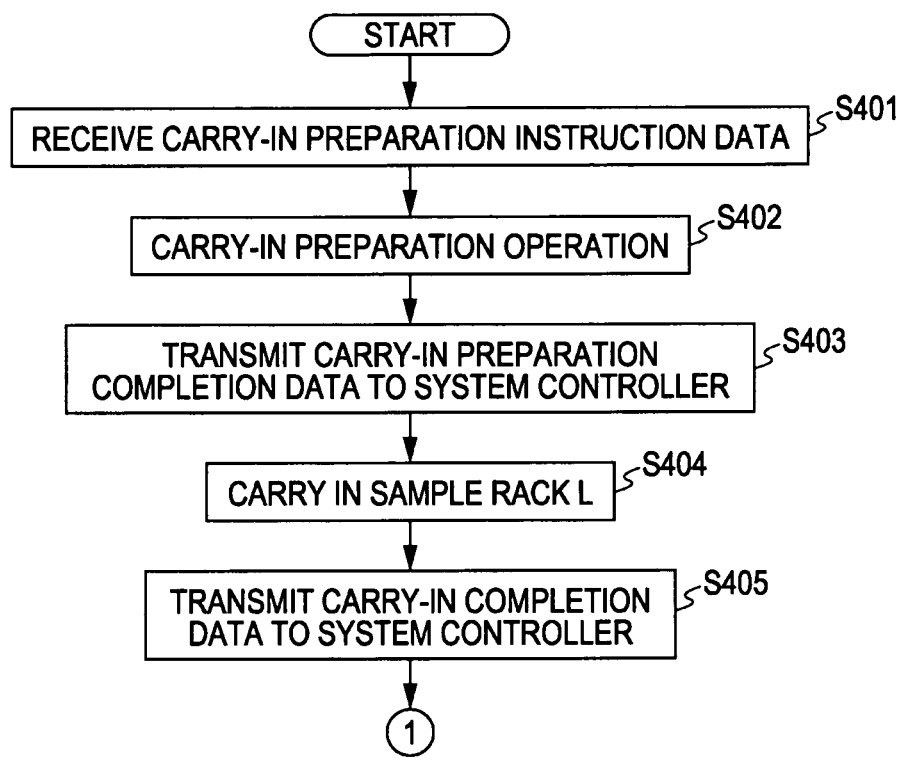
FIG. 19 is a flowchart showing a flow of the control process of the conveyance mechanism by the control unit of the sample transportation apparatus.
Figure 20:
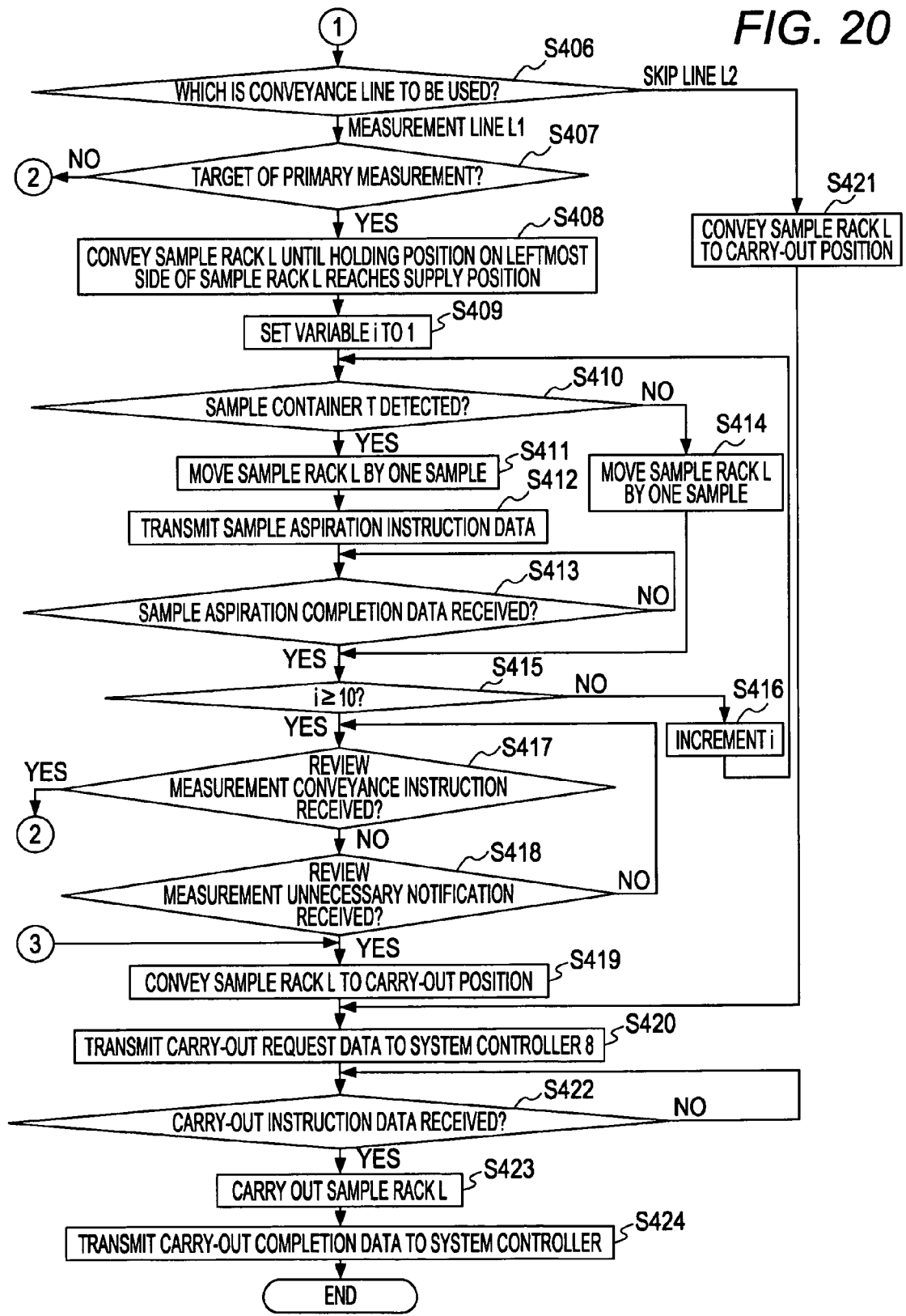
FIG. 20 is a flowchart showing a flow of the control process of the conveyance mechanism by the control unit of the sample transportation apparatus.
Figure 21:
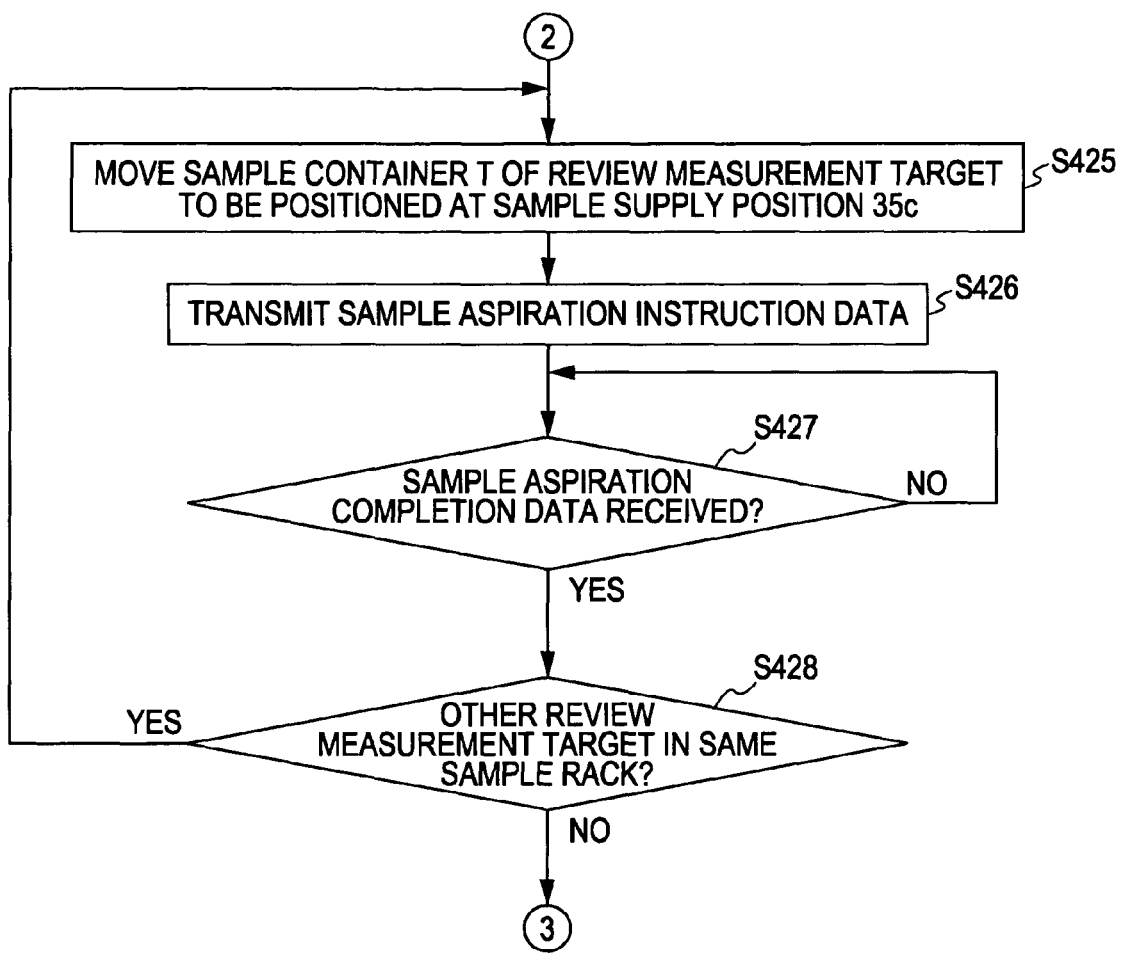
FIG. 21 is a flowchart showing a flow of the control process of the conveyance mechanism by the control unit of the sample transportation apparatus.

When a review measurement order on the sample completed with the primary measurement occurs, the system controller 8 controls the sample transportation apparatus 3 such that the sample is conveyed to the measurement unit for the review measurement. FIG. 18 is a flowchart describing a review measurement process in the CPU 81a of the system controller 8. First, the review measurement order is received from the information processing unit 52 (step S601). The received measurement order is the order of the review measurement, and thus the system controller recognizes that the sample to be conveyed is the target of review measurement. The review measurement order includes, in addition to those contained in the measurement order of primary measurement such as sample ID and patient information, the review measurement item and the information related to the measurement unit ID of the measurement unit that performed the primary measurement. The CPU 81a then determines the conveying destination of the sample (step S602). Which of M1, M2, M3 is the measurement unit for review measurement is checked based on the registered content of the measurement unit management table TBL, and the measurement unit registered for the review measurement is determined as the conveying destination of the sample. In the present example, the measurement unit M3 is registered for review measurement, and thus the measurement unit M3 is the conveying destination of the sample. The CPU 81a then transmits the conveyance instruction to the sample transportation apparatus 3 to perform the review measurement on the sample (step S602), and terminates the process. The sample rack holding the container of the sample which primary measurement is terminated and is the target of review measurement waits at the sample sending position 391 of the sample transportation apparatus 3. Therefore, if the measurement unit that performed the primary measurement is the measurement unit M3, the review measurement is performed in the same measurement unit, and thus the sample transportation apparatus 3 is controlled so that the sample rack at the sample sending position 391 is conveyed in the opposite direction and the sample container of the target of review measurement is positioned at the sample supply position 35c. If the measurement unit that performed the primary measurement is the measurement unit M1 or M2, the sample transportation apparatus 3 is controlled to convey the sample to the measurement unit M3.

<Operation of Control Unit 32 of Sample Transportation Apparatus 3>

The operation of the control unit 32 of the sample transportation apparatus 3 arranged on the front side of the measurement unit 51 will be described below. FIGS. 19, 20, 21, and 22 are flowcharts showing the flow of the control process of the conveyance mechanism 31 by the control unit 32. The carry-in preparation instruction data transmitted from the system controller 8 is received by the control unit 32 (step S401). The conveyance control program executed by the CPU of the control unit 32 is an event-driven type program, wherein the process of step S402 is called out when an event of receiving the carry-in preparation instruction data occurs in the control unit 32.

In step S402, the control unit 32 drives the belt 321a of the conveyance mechanism 31, and the like to execute the carry-in preparation operation (step S402). When the carry-in preparation is completed, the control unit 32 transmits the carry-in preparation completion data for notifying that the carry-in preparation is completed to the system controller 8 (step S403).

In response to the transmission of the carry-in preparation completion data, the sample rack L is carried out from the device of the pre-stage, and the sample rack L is carried into the conveyance mechanism 31 (step S404). When the carrying in of the sample rack L is completed, the control unit 32 transmits the carry-in completion data for notifying that the carrying in of the sample rack L is completed to the system controller 8 (step S405).

The control unit 32 determines which of the measurement line L1 or the skip line L2 the use conveyance line instruction data contained in the carry-in preparation instruction data is indicating, that is, which of the measurement line L1 or the skip line L2 is the conveyance line to be used (step S406). If the use conveyance line instruction data contained in the carry-in preparation instruction data indicates the measurement line L1, that is, if the measurement line L1 is the conveyance line to be used in step S406 ("measurement line L1" in step S406), the control unit 32 determines whether the sample accommodated in the sample container T of the sample rack L is the target of primary measurement or the target of review measurement based on the measurement order contained in the carry-in preparation instruction data (step S407). If being the target of review measurement (NO in step S407), the process advances to step S425. If being the target of primary measurement (YES in step S407), the control unit 32 controls the conveyance mechanism 31 so that the holder positioned on the leftmost side in FIG. 3 of the holders of the sample container T of the sample rack L moves until reaching the sample container detection position (step S408). The control unit 32 then sets a variable i indicating the holding position of the sample container T in the sample rack L to 1 (step S409), determines whether or not the sample container T is detected at the sample container detection position by the sample container sensor 38 (step S410), moves the sample rack L in the left direction by one sample when the sample container T is detected (YES in step S410), and transmits the sample aspiration instruction data instructing the aspiration instruction of the sample to the information processing unit 51 (step S412). The sample container T detected by the sample container sensor 38 is thereby positioned at the sample supply position 35c, and the sample is aspirated as hereinafter described. The control unit 32 waits until receiving the sample aspiration completion data (NO in step S413), and advances the process to step S415 when receiving the sample aspiration completion data (YES in step S413).

If the sample container T is not detected in step S410 (NO in step S410), the control unit 32 moves the sample rack L in the left direction by one sample (step S414), and advances the process to step S415. In step S415, the control unit 32 determines whether or not i is greater than or equal to 10 (step S415), and increments i by one (step S416) if i is less than 10 (NO in step S415), and returns the process to step S410.

If i is greater than or equal to 10 in step S415 (YES in step S415), the control unit 32 advances the process to step S417.

Steps S417, S418 of the case where the control unit 32 performing the process is of the sample transportation apparatus 3 corresponding to the measurement unit M3 will be described. In step S417, whether or not the review measurement conveyance instruction is received from the transportation controller 8 is determined (step S417). When determined that the review measurement conveyance instruction is received (YES in step S417), the process advances to step S425 (see FIG. 21). The processes from step S425 to step S428 will be hereinafter described. If determined that the review measurement conveyance instruction is not received (NO in step S417), whether or not the review measurement unnecessary notification is received from the CPU 521a of the information processing unit 52 of the blood cell analyzer 5 is determined (step S418). If determined that the review measurement unnecessary notification is received (YES in step S418), the process advances to step S419. If determined that the review measurement unnecessary notification is not received (NO in step S418), the process returns to step S417. In other words, the sample rack L is not carried out and waits near the measurement unit until either the review measurement conveyance instruction or the review measurement unnecessary notification is received.

Figure 22:
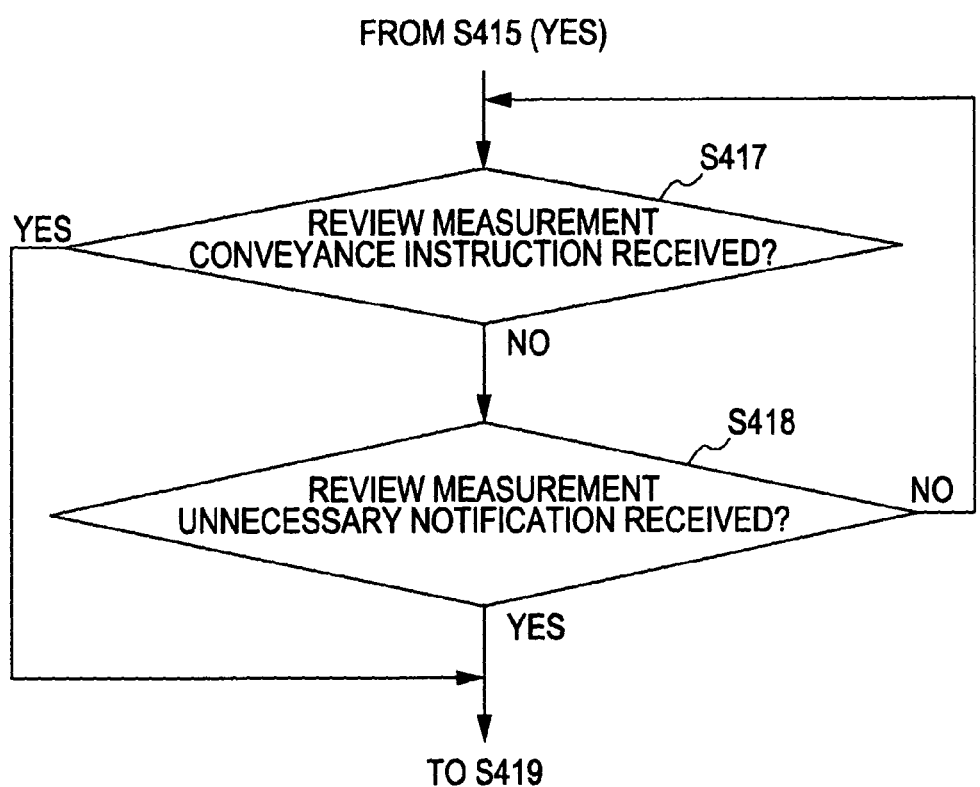
FIG. 22 is a flowchart showing a flow of the control process of the conveyance mechanism by the control unit of the sample transportation apparatus.

If the control unit 32 performing the process is of the sample transportation apparatus 3 corresponding to the measurement unit M1 or M2, the difference lies only in the process of step S417 compared to the previously described process. As shown in FIG. 22, if determined that the review measurement conveyance instruction is received in step S417 (YES in step S417), the process advances to step S419. If determined that the review measurement conveyance instruction is not received (NO in step S417), whether or not the review measurement unnecessary notification is received from the CPU 521a of the information processing unit 52 of the blood cell analyzer 5 is determined, similar to the previously described process (step S418), wherein the process advances to step S419 if determined that the review measurement unnecessary notification is received (YES in step S418), and the process returns to step S417 if determined that the review measurement unnecessary notification is not received (NO in step S418).

In step S419, the control unit 32 controls the conveyance mechanism 31 so that the sample rack L reaches the carry-out position for carrying out the sample rack L (step S419). The control unit 32 thereafter advances the process to step S420.

If the use conveyance line instruction data contained in the carry-in preparation instruction data indicates the skip line L2 in step S406, that is, if the skip line L2 is the conveyance line to be used ("skip line L2" in step S406), the control unit 32 controls the conveyance mechanism 31 so that the sample rack L moves on the skip line L2, and the sample rack L reaches the carry-out position for carrying out the sample rack L (step S421). The control unit 32 then advances the process to step S420.

In step S420, the control unit 32 transmits the carry-out request data containing the rack ID assigned to the sample rack L to the system controller 8 (step S420). Thereafter, the control unit 32 waits for the carry-out instruction data from the system controller 8 (NO in step S422), drives the stepping motor 321b to carry out the sample rack L to the adjacent sample transportation apparatus 3 (step S423) when receiving the carry-out instruction data (YES in step S422), and transmits the carry-out completion data to the system controller 8 (step S424). The control unit 32 then terminates the process.

Step S425 of the cases of being determined that the sample is the target of review measurement in step S407 (NO in step S407), and being determined that the review measurement conveyance instruction is received in step S417 (YES in step S417) will be described. In step S425, the sample rack L is moved so that the sample container T accommodating the sample of the review measurement target is positioned at the sample supply position 35c. The sample aspiration instruction data indicating the aspiration instruction of the sample is transmitted to the information processing unit 51 (step S426). The control unit 32 waits until receiving the sample aspiration completion data (NO in step S427), and advances the process to step S428 when receiving the sample aspiration completion data (YES in step S427). In step S428, whether or not other sample of review measurement target exists in the same sample rack L is determined and if determined to exist (YES in step S428), the process returns to step S425, and if determined to not exist (NO in step S428), the process advances to step S418.

<Operation of Blood Cell Analyzer 5>

The operation of the blood cell analyzer 5 will now be described. The information processing unit 52 controls the operation of the measurement units 51, 51, 51 to measure the sample, and analyzes the measurement data obtained by the measurement.

Figure 23:
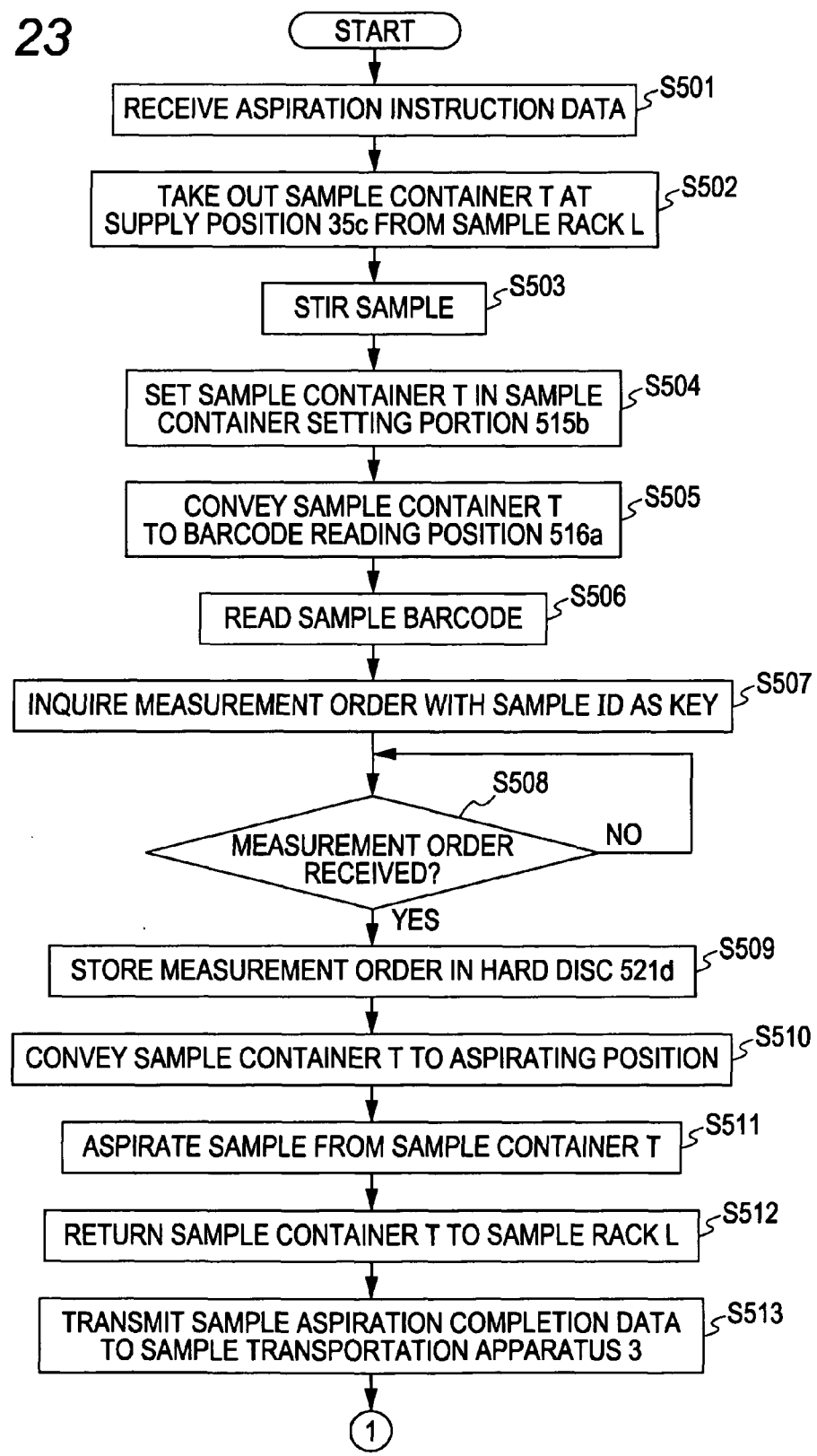
FIG. 23 is a flowchart showing a procedure of the analyzing operation of the sample by the blood cell analyzer according to the present embodiment.
Figure 24:
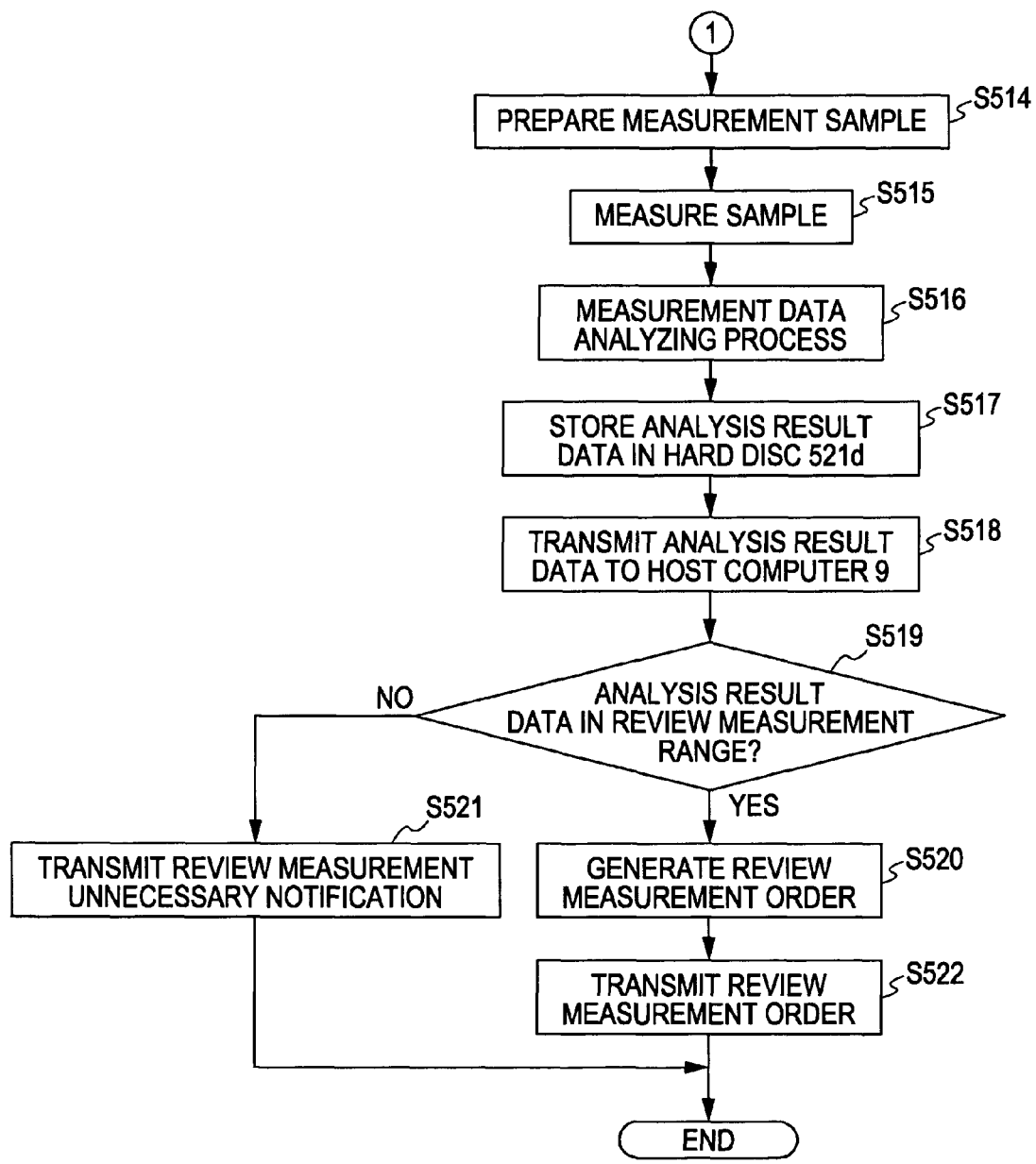
FIG. 24 is a flowchart showing a procedure of the analyzing operation of the sample by the blood cell analyzer according to the present embodiment.

FIGS. 23 and 24 are flowcharts showing the procedure of the analyzing operation of the sample by the blood cell analyzer 5 according to the present embodiment. First, the aspiration instruction data transmitted from the control unit 32 of the sample transportation apparatus 3 is received by the information processing unit 52 (step S501). In the CPU 521a, the process of step S502 is called out when an event of receiving the aspiration instruction data occurs. The aspiration instruction data includes the measurement unit ID of the measurement unit 51 to be operated.

In step S502, the CPU 521a controls the sample container conveyance portion 515, takes out the sample container T at the supply position 35c from the sample rack L (step S502), controls the hand portion 515a to oscillate the sample container T and stirs the sample inside (step S503). The CPU 521a controls the hand portion 515a to set the sample container T in the sample container setting portion 515b (step S504), and controls the sample container conveyance portion 515 to convey the sample container T to the barcode reading position 516a (step S505). The CPU 521a reads the sample barcode of the sample container T by the barcode reading portion 516 and acquires the sample ID (step S506). The CPU 521a transmits the order request data including the sample ID to the host computer 9 through the communication interface 521g (step S507), and inquires the measurement order. Thereafter, the CPU 521 waits for the reception of the measurement order (NO in step S508), when receiving the measurement order transmitted from the host computer 9 by the communication interface 521g of the information processing unit 52 (YES in step S508), stores the received measurement order in the hard disc 521d (step S509).

The CPU 521a controls the sample container conveyance portion 515 to convey the sample container T to the aspirating position (step S510), and controls the sample aspirating portion 511 to aspirate the sample of an amount necessary for the measurement item contained in the stored measurement order from the sample container T (step S511). After the aspiration of the sample is completed, the CPU 521a controls the sample container conveyance portion 515 and returns the sample container T to the sample rack L (step S512), and transmits the sample aspiration completion data to the sample transportation apparatus 3 conveying the sample rack L (step S513). The sample rack L is thereby conveyed by the rack conveyance portion 35.

The CPU 521a controls the sample preparing portion 512 to prepare the measurement sample depending on the measurement item (step S514), supplies the measurement sample to the detecting portion 513 and measures the sample by the detecting portion 513 (step S515). The CPU 521a then acquires the measurement data output from the detecting portion 513. The CPU 521a executes the analyzing process of the measurement data (step S516), classifies the blood cells contained in the sample and counts the number of blood cells for every type, and creates a scattergram in which the classified blood cells are color-coded for every type. The analysis result data generated by the analyzing process of the measurement data is stored in the hard disc 521a with the patient information and the like contained in the measurement order (step S517), and transmitted to the host computer 9 (step S518). The host computer 9 integrates the analysis result data to the measurement order and stores the same in the hard disc. The CPU 521a then compares the value of each measurement item contained in the analysis result data with a predetermined review measurement reference value, and determines whether or not the review measurement on the relevant sample is necessary (step S519). If the analysis result data is in a range requiring the review measurement, the review measurement order is generated (step S520). The review measurement item is determined based on the result of comparing the value of each measurement item contained in the analysis result data with the predetermined review measurement reference value. The review measurement order generated using such information is transmitted to the host computer 9 and the system controller 8 (step S522), and the process is terminated. If the analysis result data is not in the range requiring the review measurement in step S519 (NO in step S519), the review measurement unnecessary notification is transmitted to the control unit 32 of the sample transportation apparatus 3 through the system controller 8. The CPU 521a then terminates the process.

<Operation of Sample Transportation Apparatus 301>

The sample rack L sent from the sample transportation apparatus 3 positioned on the most downstream side in the conveying direction is introduced to the rack slider 303. The details will be omitted, but the rack slider 303 accepts the instruction from the system controller 8, and sends the sample rack L to either the measurement line 302a or the skip line 302b of the conveyor 302. When the sample rack L is carried in the measurement line 302a, the control unit of the conveyor 302 operates the measurement line 302a, and conveys the sample rack L so that the sample container T of the smear producing target is positioned at the supply position of supplying the sample to the smear producing device 6. After the supply of sample to the smear producing device 6 is completed, the measurement line 302a is further driven and the sample rack L is carried out to the sample accommodating device 4. When the sample rack L is carried in the skip line 302b, the control unit of the conveyor 302 operates the skip line 302b, conveys the sample rack L on the skip line 302b, and carries out the sample rack L to the sample accommodating device 4.

<Operation of Sample Accommodating Device 4>

The sample rack L sent out from the sample transportation apparatus 301 is introduced to the sample accommodating device 4. The sample accommodating device 4 conveys the sample rack L on the rack mounting portion, and accommodates the same.

According to the above configuration, the system controller 8 determines the conveying destination of the sample based on the registered content of the application related to each measurement unit, that is, whether for the primary measurement, or for the primary measurement and the review measurement. Therefore, the sample that is the target of the primary measurement and the sample that is the target of the review measurement can be appropriately distributed to each measurement unit, and a plurality of measurement units can be efficiently utilized.

In the above-described embodiment, the measurement unit can be registered to be used for both the primary measurement and the review measurement. Therefore, one of the plurality of measurement units may be used for the primary measurement and for the review measurement, and another measurement unit may be used for the primary measurement. All measurement units can be used for the primary measurement in which the number of processes is large and the review measurement can be performed using a measurement unit that can also be used for the review measurement when the review measurement occurs by configuring the sample processing system in the above manner.

In the above-described embodiment, the presence of the sample rack is detected at the rack conveyance portion 35 or a predetermined position on the sample transportation apparatus 3, specifically, a position near the analyzer, and the rack detection position 33a or a position where the sample rack temporarily waits before being supplied to the rack conveyance portion 35. Such detection result is used when determining the conveying destination of the sample, so that the conveying destination of the sample is prevented from concentrating at one location and the measurement process is prevented from delaying.

In the above-described embodiment, when determining the conveying destination of the sample or the target of the primary measurement, the measurement unit M3 used also for the review measurement is determined as the conveying destination only when the sample rack does not exist in both the rack conveyance portion 35 and the rack detection position 33a. In such manner, a drawback in that the sample that is the target of primary measurement is sequentially conveyed in excess to the measurement unit M3, which is the only measurement unit for review measurement, and the review measurement cannot be conducted when necessary can be avoided.

In the above-described embodiment, the measurement unit M3 on the most downstream side in the conveying direction of the sample rack by the sample transportation apparatus 3 of the plurality of measurement units is used for the review measurement. According to such configuration, the sample that is the target of review measurement as a result of conducting the primary measurement in another measurement unit can be conveyed to the measurement unit for the review measurement without going against the conveying direction of the sample in the entire sample processing system 1.

In the above-described embodiment, the application (for primary measurement, for primary measurement and review measurement, or for review measurement) of each measurement unit can be registered using the measurement unit application registration screen D and the measurement unit management table TBL. In such manner, the application assigned to the measurement unit can be easily changed by editing the registered content of the measurement unit management table TBL. For instance, if a state in which the occurrence rate of the review measurement is significantly high occurs, the radio button RB3 corresponding to the measurement unit M3 is reselected on the measurement unit application registration screen D to change the application of the measurement unit M3 for the primary measurement and for the review measurement to for the review measurement. Accordingly, the measurement unit M3 can be used only for the review measurement, and the process can be efficiently performed even if the sample that is the target of review measurement is in great number. Furthermore, when the measurement unit M3 breaks down and cannot be used, the radio button RB2 is reselected on the measurement unit application registration screen D with respect to the measurement unit M2 to re-register as for the primary measurement and for the review measurement. Accordingly, the measurement unit M1 can be used only for the primary measurement, and the measurement unit M2 can be used for the primary measurement and for the review measurement.

In the above-described embodiment, three measurement units 51, 51, 51 are arranged for a plurality of measurement units (analyzer) arranged along the transportation apparatus, but the number of measurement units to be arranged is not limited thereto. Two measurement units may be arranged, wherein one measurement unit may be used only for the primary measurement and the other measurement may be used for the primary measurement and the review measurement. Alternatively, four or more measurement units may be arranged, wherein one of the measurement units may be used for the primary measurement and the review measurement, and the other measurement units may be used only for the primary measurement.

In the above-described embodiment, the configurations of the three measurement units 51, 51, 51 are the same, but this is not the sole case. The sample processing system may include a plurality of measurement units having a common measurement item and different configurations.

In the above-described embodiment, an example in which three measurement units 51, 51, 51 and the information processing device 52 configure the blood cell analyzer 5 has been described, but the present invention is not limited thereto. Each measurement unit may include the respective information processing unit. The sample processing system may include a plurality of separate analyzers.

In the above-described embodiment, a configuration in which the sample processing system 1 includes the blood analyzer 5 for classifying the blood cells contained in the sample and counting the blood cells for every blood cell type has been described above, but this is not the sole case. The sample processing system may include a plurality of measurement units of a sample analyzer other than the blood cell analyzer such as the immune analyzer, the blood coagulation measurement device, the biochemical analyzer, and the urine analyzer, so that the blood sample or the urine sample is conveyed to the measurement unit of the relevant sample analyzer.

In the above-described embodiment, a configuration of determining the conveying destination of the sample rack L by having the CPU 81*a* of the system controller 8 execute the program for system control has been described, but this is not the sole case. A configuration of executing the process of determining the conveying destination of the sample rack L by a dedicated hardware such as FPGA or ASIC capable of executing the process similar to the conveying destination determination program of the sample rack L may be adopted.

In the above-described embodiment, a configuration of executing all processes of the computer program 84*a* by the single computer 8*a* has been described, but the present invention is not limited thereto, and a distributed system of distributing the processes similar to the computer program 84*a* to a plurality of devices (computers) and executing the programs may be adopted.

What is claimed is:

1. Sample processing system comprising:
   a plurality of transportation apparatuses configured to convey a sample container, including a first transportation apparatus connected to a second transportation apparatus;
   a first analyzer, arranged along the first transportation apparatus, configured to measure a sample accommodated in a sample container that has been conveyed by the first transportation apparatus;
   a second analyzer, arranged along the second transportation apparatus, configured to measure the sample accommodated in the sample container that has been conveyed by the second transportation apparatus; and
   a transportation controller configured to
      receive input indicating a selection of an application of the first analyzer from a first set of applications available for the first analyzer, including (i) primary measurement and not review measurement, (ii) primary measurement and review measurement, and (iii) review measurement and not primary measurement, and a selection of an application of the second analyzer from a second set of applications available for the second analyzer, including (i) primary measurement and not review measurement, (ii) primary measurement and review measurement, and (iii) review measurement and not primary measurement,
      in response to receiving the input, register in a memory of the transportation controller the selected application of the first analyzer and the selected application of the second analyzer,
      determine a target analyzer to which the sample container is conveyed based on the selected application of the first analyzer and the selected application of the second analyzer registered in the memory, and
      control at least one of the first and second transportation apparatuses to convey the sample container to the target analyzer.

2. The sample processing system according to claim 1, wherein the transportation controller is configured to receive a measurement order and recognize if the sample in the sample container is a target of primary or review measurement based on the measurement order, wherein the transportation controller is configured to determine a target analyzer to which the sample container is conveyed as the second analyzer when the sample in the sample container is the target of review measurement, the selected application of the first analyzer is the application (i), and the selected application of the second analyzer is the application (ii) or (iii).

3. The sample processing system according to claim 1, wherein the transportation controller is configured to receive a measurement order and recognize if the sample in the sample container is a target of primary or review measurement based on the measurement order, wherein the transportation controller is configured to determine a target analyzer to which the sample container is conveyed as the first or the second analyzer when the sample in the sample container is the target of primary measurement, the selected application of the first analyzer is the application (i) or (ii), and the selected application of the second analyzer is the application (i) or (ii).

4. The sample processing system according to claim 3 further comprising an information processing unit communicably connected to the transportation controller and configured to control the first analyzer to conduct the primary measurement on the sample when the sample is the target of primary measurement and the sample container accommodating the sample is conveyed to the first analyzer of the first and second analyzers.

5. The sample processing system according to claim 4, wherein the transportation controller is configured to recognize if the sample in the sample container is a target of review measurement after the primary measurement, wherein the transportation controller is configured to control the first and second transportation apparatuses to convey the sample container from the first analyzer to the second analyzer when the sample is the target of review measurement after the primary measurement, the selected application of the first analyzer is the application (i), and the selected application of the second analyzer is the application (ii) or (iii).

6. The sample processing system according to claim 3 further comprising an information processing unit communicably connected to the transportation controller and configured to control the second analyzer to conduct the primary measurement on the sample when the sample is the target of primary measurement and the sample container accommodating the sample is conveyed to the second analyzer of the first and second analyzers.

7. The sample processing system according to claim 6, wherein the transportation controller is configured to recognize if the sample in the sample container is a target of review measurement after the primary measurement, wherein the transportation controller is configured to control the first and second transportation apparatuses to convey the sample container to a position where the second analyzer acquires the sample when the sample is the target of review measurement after the primary measurement and the selected application of the second analyzer is the application (ii).

8. The sample processing system according to claim 7, wherein the transportation controller is configured to control the first and second transportation apparatuses to have the sample container accommodating the sample after the primary measurement wait near the second analyzer after the primary measurement and before recognizing if the sample is the target of review measurement.

9. The sample processing system according to claim 1, wherein the second analyzer is positioned on a downstream side in a conveying direction of the sample container by the transportation apparatuses with respect to the first analyzer.

10. The sample processing system according to claim 1, wherein
each respective transportation apparatus of the plurality of transportation apparatuses comprises a detector for detecting whether or not the sample container exists at a predetermined position on the respective transportation apparatus; and
the transportation controller is configured to determine an analyzer from among the first analyzer and the second analyzer that is to be a conveying destination of the sample container to convey based on a detection result of the detector of at least one of the transportation apparatuses.

11. The sample processing system according to claim 10, wherein the predetermined position is a first position near the first analyzer or a second position for temporarily holding the sample container before supplying the sample container to the first position.

12. The sample processing system according to claim 10, wherein the predetermined position is a first position near the second analyzer or a second position for temporarily holding the sample container before supplying the sample container to the first position.

13. The sample processing system according to claim 1, wherein the transportation controller is configured to receive a measurement order related to the sample to be conveyed.

14. The sample processing system according to claim 13, wherein the transportation controller is configured to determine a target analyzer to which the sample is conveyed as the second analyzer if the measurement order is an order of review measurement, the selected application of the first analyzer is the application (i), and the selected application of the second analyzer is the application (ii) or (iii).

15. The sample processing system according to claim 13, wherein the transportation controller is configured to determine a target analyzer to which the sample is conveyed as the first or the second analyzer if the measurement order is an order of primary measurement, the selected application of the first analyzer is the application (i) or (ii), and the selected application of the second analyzer is the application (i) or (ii).

16. The sample processing system according to claim 1, wherein
the first transportation apparatus comprises a first transport unit which transports the sample container to the first analyzer and the second transportation apparatus comprises a second transport unit which is connected to the first transport unit and transports the sample container received from the first transport unit to the second analyzer,
each of the first and second transport units is configured to transport the sample container along a transport path in a first direction and along the transport path in a second direction opposite to the first direction,
the transportation controller is configured to receive a measurement order and determine if the sample in the sample container is a target of primary or review measurement based on the measurement order,
when the selected application of the second analyzer registered in the memory is the application (ii) and when the sample in the sample container is determined to be a target of primary measurement and the sample container is transported to the transport path of the second transport unit, the transportation controller is configured to control the second transport unit to transport the sample container located on the transport path of the second transport unit in the first direction to convey the sample container to a supply position for supplying the sample to the second analyzer,
after the second analyzer has measured the sample in the sample container, the transportation controller is configured to control the second transport unit to have the sample container wait at a waiting position on the transport path of the second transport unit, the waiting position being located on a downstream side of the supply position in the first direction, and
in response to a determination that the sample is the target of review measurement, the transportation controller is configured to control the second transport unit to transport the sample container from the waiting position in the second direction to convey the sample container to the supply position.

17. The sample processing system according to claim 16, wherein
when the selected application of the first analyzer registered in memory is the application (i) and the selected application of the second analyzer registered in the memory is the application (ii) or (iii) and when the sample in the sample container is determined to be a target of primary measurement and the sample container is transported to the transport path of the first transport unit, the transportation controller is configured to control the first transport unit to transport the sample container located on the transport path of the first transport unit in the first direction to convey the sample container to a supply position for supplying the sample to the first analyzer,
after the first analyzer has measured the sample in the sample container, the transportation controller is configured to control the first transport unit to have the sample container wait at a waiting position on the transport path of the first transport unit, the waiting position being located on a downstream side of the supply position in the first direction, and
in response to a determination that the sample is the target of review measurement, the transportation controller is configured to control the first transport unit to transport the sample container from the waiting position to the second transport unit.

18. The sample processing system according to claim 16, wherein
each transport path of the first and second transport units is configured to transport a sample rack holding a plurality of sample containers, including the sample container accommodating the sample determined to be the target of primary or review measurement by the transportation controller, when the selected application of the second analyzer registered in the memory is the application (ii) and when the sample in the sample container is determined to be a target of primary measurement and the sample rack is transported to the transport path of the second transport unit, the transportation controller is configured to control the second transport unit to transport the sample rack located on the transport path of the second transport unit in the first direction to convey the sample container to the supply position, after the second analyzer has measured the sample in the sample container, the transportation controller is configured to control the second transport unit to have the sample rack wait at the waiting position, and in response to a determination that the sample is the target of review measurement, the transportation controller is configured to control the second transport unit to transport the sample rack from the waiting position in the second direction to convey the sample container to the supply position.

19. A sample processing system comprising:
a plurality of transportation apparatuses configured to convey a sample container, including a first transportation apparatus connected to a second transportation apparatus;
a first analyzer, arranged along the first transportation apparatus, configured to measure a sample accommodated in a sample container that has been conveyed by the first transportation apparatus;
a second analyzer, arranged along the second transportation apparatus, configured to measure the sample accommodated in the sample container that has been conveyed by the second transportation apparatus; and
a transportation controller configured to
receive input indicating a selection of an application of the first analyzer from a first set of applications available for the first analyzer, including (i) primary measurement and not review measurement, (ii) primary measurement and review measurement, and (iii) review measurement and not primary measurement, and a selection of an application of the second analyzer from a second set of applications available for the second analyzer, including (i) primary measurement and not review measurement, (ii) primary measurement and review measurement, and (iii) review measurement and not primary measurement,
in response to receiving the input, assign the selected application of the first analyzer to the first analyzer and the selected application of the second analyzer to the second analyzer,
receive a measurement order related to the sample and recognize if the sample in the sample container is a target of primary or review measurement based on the measurement order,
determine a target analyzer to which the sample container is conveyed based on the assigned application of the first analyzer and the assigned application of the second analyzer, and
control at least one of the first and second transportation apparatuses to convey the sample container to the target analyzer, wherein
the transportation controller is configured to determine a target analyzer to which the sample container is conveyed as the first or the second analyzer when the assigned application of the first analyzer is the application (i) or (ii), the assigned application of the second analyzer is the application (i) or (ii) and the sample accommodated in the sample container is a target of primary measurement, and
the transportation controller is configured to determine a target analyzer to which the sample container is conveyed as the second analyzer when the assigned application of the first analyzer is the application (i), the assigned application of the second analyzer is the application (ii) or (iii) and the sample accommodated in the sample container is a target of review measurement.

20. The sample processing system according to claim 19, wherein the transportation controller comprises a memory for storing the assigned application of the first analyzer and the assigned application of the second analyzer.

21. A controlling method of a transportation apparatus in a sample processing system comprising a plurality of transportation apparatuses for conveying a sample container, a first analyzer, arranged along a first transportation apparatus, configured to measure a sample accommodated in a sample container that has been conveyed by the first transportation apparatus, a second analyzer, arranged along a second transportation apparatus, configured to measure the sample accommodated in the sample container that has been conveyed by the second transportation apparatus, and a transportation controller for controlling the conveying operation of the sample container by at least one of the first and second transportation apparatuses, the method comprising steps of:
receiving, by the transportation controller, input indicating a selection of an application of the first analyzer from a first set of applications available for the first analyzer, including (i) primary measurement and not review measurement, (ii) primary measurement and review measurement, and (iii) review measurement and not primary measurement and a selection of an application of the second analyzer from a second set of applications available for the second analyzer, including (i) primary measurement and not review measurement, (ii) primary measurement and review measurement, and (iii) review measurement and not primary measurement,
in response to receiving the input, storing, by the transportation controller, the selected application of the first analyzer and the selected application of the second analyzer;
receiving an order of the primary measurement or an order of the review measurement related to the sample accommodated in the sample container at the transportation controller;
determining an analyzer to which the sample is conveyed based on the selected application of the first analyzer and the selected application of the second analyzer stored by the transportation controller in the storing step and the order of measurement received by the receiving step; and
controlling at least one of the first and second transportation apparatuses to convey the sample container to the analyzer determined in the determining step.

* * * * *